(12) United States Patent
Sachs et al.

(10) Patent No.: US 11,917,250 B1
(45) Date of Patent: Feb. 27, 2024

(54) AUDIOVISUAL CONTENT SELECTION

(71) Applicants: Dan Sachs, Minneapolis, MN (US); Dwight E. Nelson, Shoreview, MN (US)

(72) Inventors: Dan Sachs, Minneapolis, MN (US); Dwight E. Nelson, Shoreview, MN (US)

(*) Notice: Subject to any disclaimer, the term of this patent is extended or adjusted under 35 U.S.C. 154(b) by 0 days.

(21) Appl. No.: 17/935,499

(22) Filed: Sep. 26, 2022

Related U.S. Application Data

(63) Continuation of application No. 16/824,078, filed on Mar. 19, 2020, now abandoned.

(Continued)

(51) Int. Cl.
| | |
|---|---|
| *H04N 21/472* | (2011.01) |
| *H04N 21/466* | (2011.01) |
| *H04N 21/81* | (2011.01) |
| *G16H 20/70* | (2018.01) |
| *A61B 5/16* | (2006.01) |
| *A61M 21/00* | (2006.01) |
| *A61B 5/00* | (2006.01) |

(52) U.S. Cl.
CPC ........... *H04N 21/472* (2013.01); *A61B 5/165* (2013.01); *A61B 5/7267* (2013.01); *A61M 21/00* (2013.01); *G16H 20/70* (2018.01); *H04N 21/4667* (2013.01); *H04N 21/8106* (2013.01); *A61M 2021/0027* (2013.01); *A61M 2021/0044* (2013.01)

(58) Field of Classification Search
CPC ...... G16H 20/70; A61B 5/165; A61B 5/7267; A61M 21/00; A61M 2021/0027; A61M 2021/0044; H04N 21/472; H04N 21/4667; H04N 21/8106
See application file for complete search history.

(56) References Cited

U.S. PATENT DOCUMENTS

| | | | |
|---|---|---|---|
| 5,711,671 A | 1/1998 | Geeslin et al. | |
| 5,725,472 A * | 3/1998 | Weathers | A61M 21/0094 600/545 |

(Continued)

FOREIGN PATENT DOCUMENTS

CN    101934111 A    1/2011

OTHER PUBLICATIONS

U.S. Appl. No. 16/824,078, Advisory Action dated Aug. 17, 2022, 3 pgs.

(Continued)

*Primary Examiner* — Eddy Saint-Vil
(74) *Attorney, Agent, or Firm* — Schwegman Lundberg & Woessner, P.A.

(57) ABSTRACT

Systems and techniques are disclosed for aspects of audiovisual content selection based on collecting and processing physiological data. In an example, a system comprises: a sensor device with at one physiological sensor to capture physiological data from a human subject; an output device with a display device to output video and a speaker to output audio to the human subject; and a computing device with at least one processor to control an output of digital audiovisual data to a human subject via the output device, based on data processing operations including a comparison of an observed pattern of autonomic nervous system activity to a target pattern of autonomic nervous system activity.

20 Claims, 18 Drawing Sheets

Related U.S. Application Data

(60) Provisional application No. 62/821,913, filed on Mar. 21, 2019.

(56) References Cited

U.S. PATENT DOCUMENTS

| | | |
|---|---|---|
| 6,293,904 B1 | 9/2001 | Blazey et al. |
| 6,425,764 B1 | 7/2002 | Lamson |
| 2004/0152957 A1 | 8/2004 | Stivoric et al. |
| 2007/0100666 A1 | 5/2007 | Stivoric et al. |
| 2008/0318678 A1 | 12/2008 | Stivoric et al. |
| 2010/0234671 A1 | 9/2010 | Brandes |
| 2011/0213197 A1 | 9/2011 | Robertson et al. |
| 2012/0313746 A1* | 12/2012 | Rahman .............. G06F 15/00 340/5.1 |
| 2014/0307878 A1 | 10/2014 | Osborne et al. |
| 2016/0180722 A1* | 6/2016 | Yehezkel .............. G09B 5/00 434/236 |
| 2017/0092331 A1* | 3/2017 | Eppolito .......... H04N 21/47205 |
| 2017/0220956 A1 | 8/2017 | Stephens et al. |
| 2017/0365101 A1 | 12/2017 | Samec et al. |
| 2018/0018540 A1* | 1/2018 | Hazur .................. G09B 7/04 |
| 2018/0068577 A1 | 3/2018 | Javanbakht |
| 2018/0096244 A1 | 4/2018 | Mallinson |
| 2019/0102706 A1 | 4/2019 | Frank et al. |
| 2020/0057661 A1* | 2/2020 | Bendfeldt .............. G06V 40/70 |
| 2020/0135039 A1* | 4/2020 | Karna .................. G06V 40/174 |
| 2020/0301965 A1* | 9/2020 | Cormican ........... G06F 3/04883 |
| 2020/0302825 A1 | 9/2020 | Sachs et al. |
| 2021/0113149 A1 | 4/2021 | Abrahami et al. |

OTHER PUBLICATIONS

U.S. Appl. No. 16/824,078, Examiner Interview Summary dated Jul. 14, 2022, 3 pgs.

U.S. Appl. No. 16/824,078, Final Office Action dated Apr. 27, 2022, 40 pgs.

U.S. Appl. No. 16/824,078, Non Final Office Action dated Aug. 19, 2021, 23 pgs.

U.S. Appl. No. 16/824,078, Response filed Feb. 16, 2022 to Non Final Office Action dated Aug. 19, 2021, 16 pgs.

U.S. Appl. No. 16/824,078, Response filed Aug. 11, 2022 to Final Office Action dated Apr. 27, 2022, 11 pgs.

\* cited by examiner

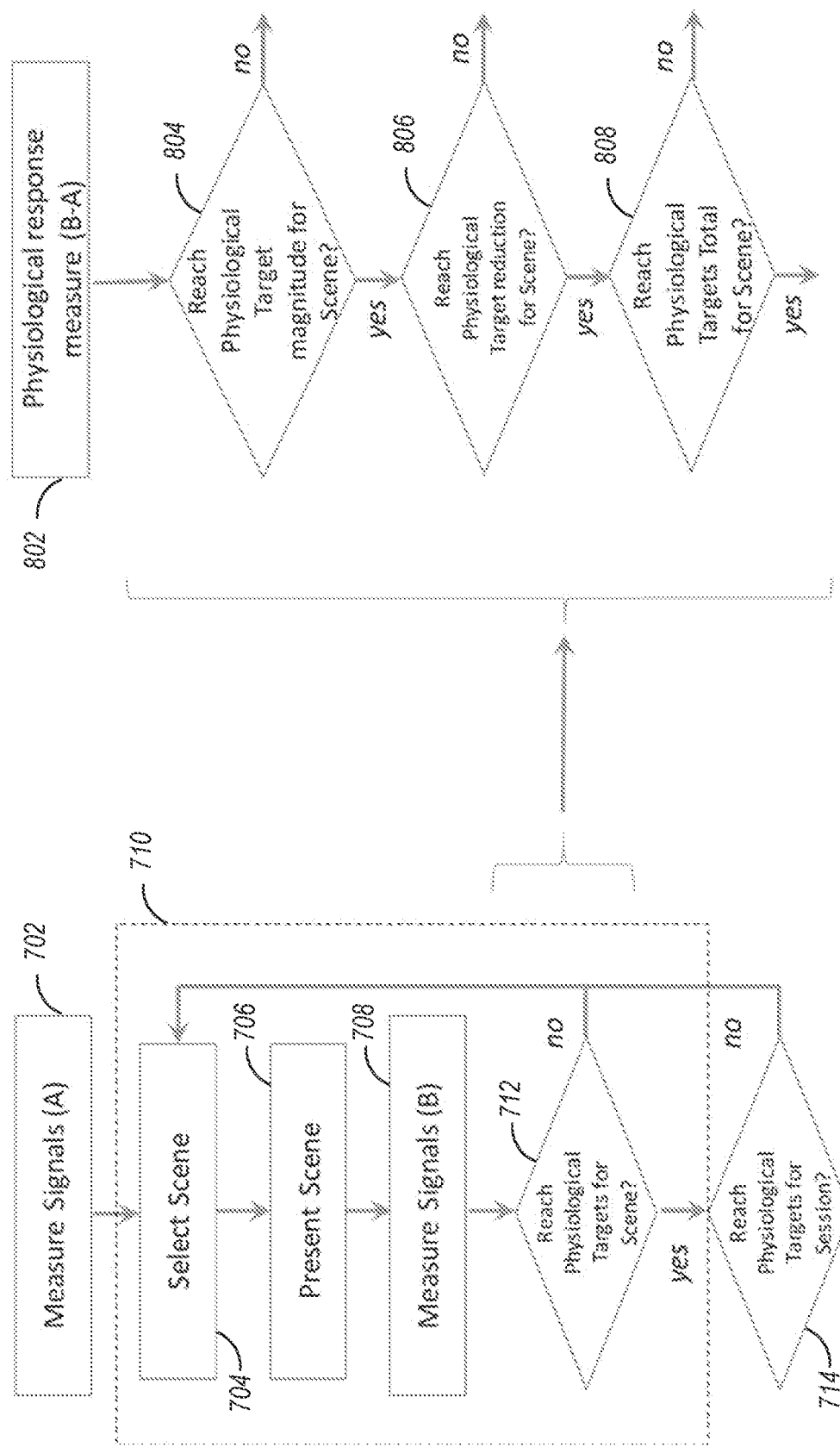

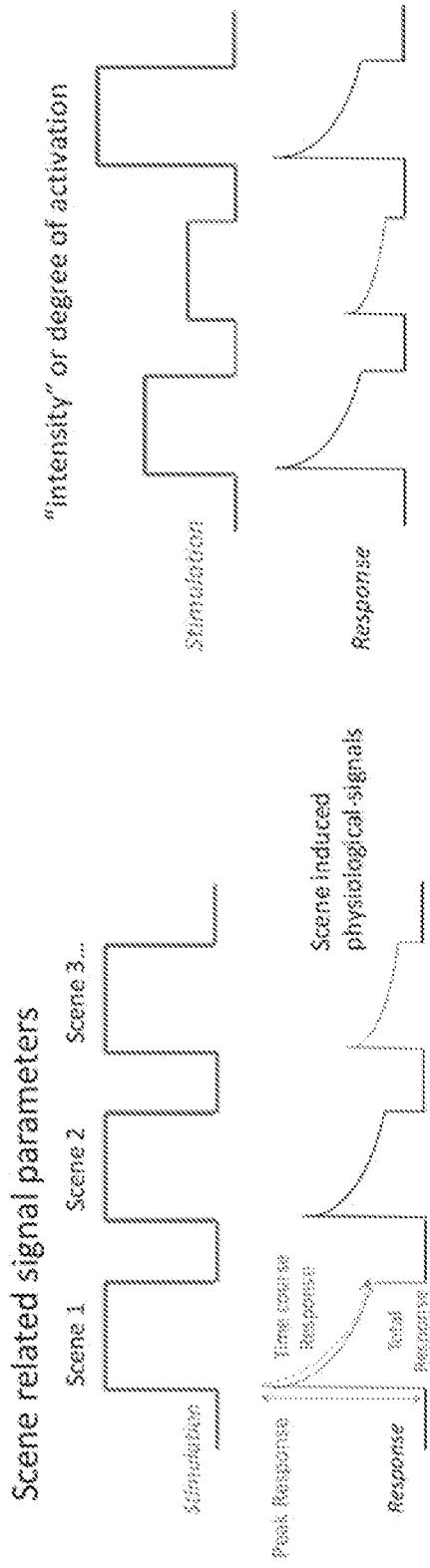
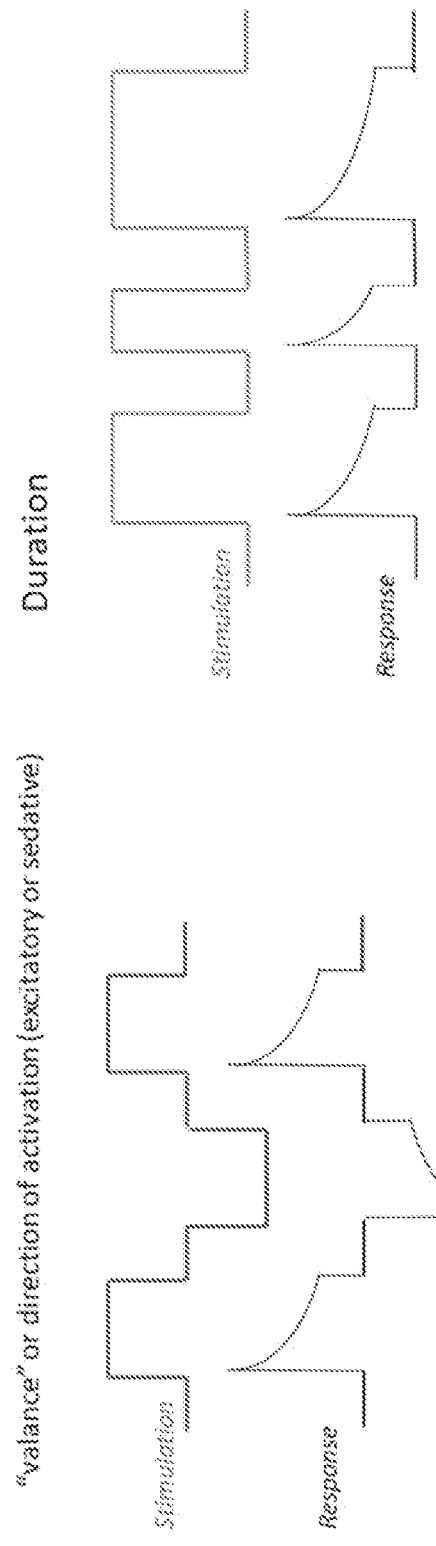
FIG. 14A
FIG. 14B
FIG. 14C
FIG. 14D

AUDIOVISUAL CONTENT SELECTION

CROSS-REFERENCE TO RELATED APPLICATIONS

This application is a continuation of and claims the benefit of priority under 35 U.S.C. § 120 to U.S. patent application Ser. No. 16/824,078, filed on Mar. 19, 2020, which application claims the benefit of priority under 35 U.S.C. § 119(e) to U.S. Patent Application Ser. No. 62/821,913, filed on Mar. 21, 2019, each of which is incorporated by reference herein in its entirety.

TECHNICAL FIELD

The present disclosure relates generally to the selection of audiovisual content based on the analysis of data from physiologic sensors, in connection with various data processing use cases.

BACKGROUND

The autonomic nervous system is a specialized set of output pathways that provide critical control of peripheral organ systems in the human body. This system is responsible for control of peripheral organ functions such as breathing, digestion, metabolism, immune function, cardiac and circulatory functions, endocrine activity, vasomotor activity, reproductive functions, menstruation, sexual arousal, and pupillary response, including certain reflexive events such as startle response, eye-blink response, coughing, sneezing, swallowing, micturition, sexual function and vomiting. At the periphery the autonomic nervous system is composed of two distinct neural output circuits: the sympathetic nervous system and the parasympathetic nervous system. These distinct output pathways are anatomically and functionally separate and control peripheral organ systems (muscles and glands) in a complementary manner. Central activation of the sympathetic nervous system generally enhances functional responses in organs linked with "fight-or-flight" such as vigilance, anxiousness, physical activity, or sexual function, while inhibiting functional responses related to "rest-and-digest" activities including satiation, calmness and activities related to routine body maintenance. In a complementary fashion, activation of the parasympathetic system inhibits fight-or-flight functions and enhances rest-and-digest functions.

These autonomic output pathways are controlled by the central nervous system in three manners including reflexive control through sensory-motor loops in spinal circuits, homeostatic control through the brain's hypothalamus and brainstem, and by complex, higher-order "cognitive-level" control through the hippocampus, limbic structures (including the amygdala) and cerebral cortex. Complex interplay among these three control loops ultimately determines the normal, balanced, dynamic and even pathological functional activities of organ systems, and responses or reactions of these systems to normal and extreme perturbations including daily and seasonal changes in the internal and external environment. Functional activity of these control loops can be monitored via markers of sympathetic-parasympathetic nervous system activity, and markers of sympathetic-parasympathetic nervous system balance, for use in a variety of applications, including physiological and psychological therapies.

Diagnosis and monitoring of medical pathologies have typically focused on dysfunctions of the reflexive or homeostatic-level control systems that drive peripheral changes in physiology and organ function. The influence of cognitive-level control systems (including brain control systems) related to psychological, psychosocial, stress, or emotional state, are more difficult to monitor.

SUMMARY

Recent improvements in physiological monitoring as well as development of audio-video content delivery methods and computer-synchronized physiological and behavioral data acquisition and methods of analysis systems and large data sets have allowed for development of new techniques and devices to assess the higher-order control systems that are associated with psychological functions and disorders. Monitoring of organ level physiology and linking physiological changes with specific nervous system stimulations can quantify the functional state of brain cognitive systems in humans.

In various examples, nervous system stimulation could be provided in the form of a auditory sensory stimulus, including one or more of the following: audio, auditory stimulation, noise, loud noise, sound, sounds, music, song, songs, song list, musical pieces, a sequence of beats, rhythm, tones, chords, spoken words, audiobooks, poetry, meditations, narratives, a recorded therapy session, volume, dynamic range, timbre, frequency, musical genre, artist, singer vocal range or voice type or native language, composer, title, lyrics, chorus, length, consonance, timbre, tempo, orchestration, instruments, volume, dynamics, instrumentation, key, key changes or transitions, pitch, frequency, frequencies, tonality (major, minor, atonal), harmony, rhythm, syncopation, time signature, phrase length, phrase shape (arch, spiky), phrase structure or shape or length, Form (binary, ternary), ritornello, repeated baseline, number of tracks or instruments or voices; or other stimuli of hearing.

In various examples, stimulation could be provided in the form of a stimulus including one or more of: vestibular, equilibrium, static or dynamic equilibrium, rotational equilibrium, balance, gravity, gravitational equilibrium, head position, head movement, motion, body motion, body position, or other stimuli of proprioception.

In various examples, stimulation could be provided in the form of one or more of: light, lighting, light patterns, flash, shade, darkness, colors, wavelengths, images, imagery, photos, video, videos, video clips, movies, optics, written material, internet content, or other visual or nonvisual stimuli of the visual system, including in connection with audio-visual content, virtual reality, and augmented reality.

In various examples, stimulation may be provided from tactile, pressure, light pressure, deep pressure, vibration, itch, pain, nocioceptive or neuropathic, stretch, muscle contraction, hair follicle position, mechanical, mechanosensory, air pressure, electrical, peripheral nerve stimulation, or other stimuli of the somatosensory system; from thermal stimulation, such as temperature, thermal or temperature levels or changes; olfactory, such as scent, smells including fragrant, fruity, citrus, woody, resinous, chemical, sweet, minty, toasted, nutty, pungent, decayed, vomit or sickening scents, or other stimuli of the olfactory system; gustatory, such as taste including sweet, salty, sour, bitter, or unami, chemosensory, or chemical. Additionally, the sensory stimulus could be delivered using visceral, interoceptive, internal startle, air pressure pulses, or other modalities; or via electrical, magnetic, electromagnetic, microwave, ultrasound, ultrasonic, radio, radiofrequency, mechanical, chemical, drug or other stimulation of sensory receptors. These modalities, as well as pharmaceuticals, implanted devices, or neurostimulation, devices could be used to induce sensory stimulation, delivered percutaneously, transcutaneously across the body surface, or using non-contact or external methods of stimulation delivery.

Sensory stimulus could be induced via exercise, or games where players must obey a stream of instructions such as Simon Says or similar techniques. Sensory stimulus could be induced via surgical manipulations or ablations or through other means including short term treatments or chronically delivered therapies and their combinations. The sensory stimulus may be delivered as a single stimulus or together or sequentially with one or more other stimuli via computer, laptop, tablet, mobile phone or other external device, speaker, smart speaker, monitor, screen, glasses, goggles, headphones, active garments, wearable devices, furniture, electronic/digital generators, or guided meditation or visualization.

In the various examples discussed herein, physiological response signals may be based on at least one of: heart rate, heart rate variability, low-frequency heart rate variability spectral power [0.04~0.15 Hz], high-frequency heart rate variability spectral power [0.15~0.4 Hz], ratio of low- to high-frequency power, blood pressure, diastolic blood pressure, systolic blood pressure, pulse pressure, blood volume pulse, pulse transit time, pulse wave velocity, blood pressure shape, waveform or pattern, baroreflex sensitivity, baroreceptor response, arterial wall stiffness, vascular elasticity, vascular tone, changes in vascular tone, markers of changes in vascular tone, orthostatic hemodynamic response, respiratory rate, respiratory sinus arrhythmia, respiratory pattern including regularity, depth, frequency, and increases and decreases in these measures over time including abrupt gasps or similar changes in breathing pattern, sympathetic nerve activity, micro-neurography, skin galvanic response, skin conductance, skin conductance level, skin conductance response, galvanic skin resistance, galvanic skin potential, electrodermal response, pilomotor reflex, pilomotor erection or goose bumps, shivering, trembling, pupil diameter, pupillary response, accelerometer or video based measurements of body, eyes and pupillary response and eye or peri-orbital musculature activities, extra-ocular muscle activities, eye movement, eye tracking to monitor fixation location and micro movements, saccade or saccades, eye blink induced by startle, eye blink rate or intensity or duration, startle response, startle reflex, exploratory behaviors, peripheral blood flow, peripheral blood flow changes, flushing, skin blood perfusion, superficial blood flow changes, skin blood perfusion changes, facial expressions (suggesting one or more of happiness, sadness, fear, disgust, anger, or surprise), imaging of facial expression, eye widening, mouth changes, skin temperature, muscle tone, muscle contraction, electromyography (EMG) of musculature including facial, cranial, neck, torso and limb as well as axial musculature, postural changes, head movements, body movements, body sway, body sway changes, hand or forearm shaking or trembling, EMG or mechanomyography (MMG) or accelerometer or imaging or other motion capture methods of limb shaking or trembling, lurching or jumping, startle response, startle reflex, freezing of movement, bradykinesia, bradykinesis, muscle stiffness, changes in posture or movement, speech pattern, changes in speech patterns such as pauses, stuttering, halting, quivering, vocal trembling, shaky voice, voice volume, or quiet voice, or changes in voice pitch or enunciation, EEG signals at different scalp regions in different frequency bands: delta (1-4 Hz), theta (4-8 Hz), alpha (8-12 Hz), beta (12-30 Hz) and gamma (30-40 Hz), EEG resting frontal activity, alpha, beta, theta, gamma or alpha-theta brain EEG ranges or their relationships, sleep quality, sleep disturbance, sleep changes, blood or serum or urine or salivary or sweat or cerebrospinal fluid biochemical markers of stress including levels or changes in levels in endocrine, neuroendocrine, neurotransmitter, neurotropic immunologic or genetic substances such as glucose, insulin, growth hormone, cortisol, corticotropin-releasing hormone (CRH), dehydroepiandrosterone (DIIEAS), adrenaline, epinephrine, norepinephrine, acetylcholine, C-reactive protein, markers of inflammation, nerve growth factor (NGF), BDNF, cytokines, pro-inflammatory cytokines such as tumor necrosis factor (TNF), TNF-α, interleukin-1 (IL-1), interleukin-6 (IL-6), interleukin, alpha melanocyte stimulating hormone, lymphocyte, natural killer cell activity, symptom or symptoms.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIG. 7 is a flowchart of an example measurement and evaluation operation flow for presenting scenes, as part of a therapy session, according to an example.

FIG. 8 is a flowchart of an operation flow for evaluating scene presentation based on a physiological response, according to an example.

FIGS. 14A to 14D illustrate a charting of example characteristics of physiological signals relative to scenes, according to an example.

DETAILED DESCRIPTION

Figure 1A:
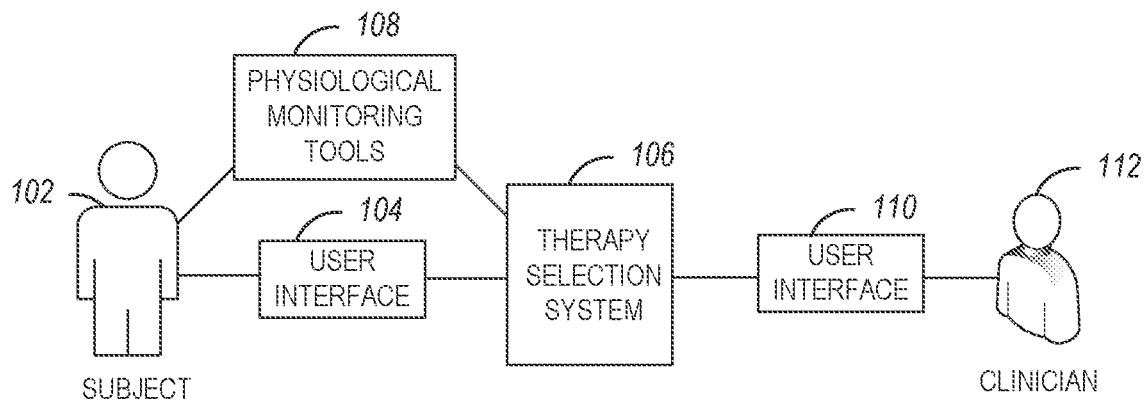
FIGS. 1A and 1B illustrate, by way of example, a use case overview of a therapy selection system, according to an example.

This document discusses various techniques, applicable in therapeutic, commercial, entertainment and training settings and scenarios, which involve stimulation to induce a target pattern of sympathetic or parasympathetic nervous system activity or balance that represents a psychological state including cognitive states, vigilance states, arousal, interest level, desirability, appeal or revulsion, repulsion, or emotional valence or affect. Within the following discussion, the terms "physiologic response signal" and "physiologic response" may be used interchangeably. Within the following discussion, delivery of a sensory stimulus and sensory stimulation may be used interchangeably.

The following device and methods proposed facilitate the quantitative assessment of autonomic nervous system activity and automated selection of appropriate sensory stimulation to achieve target levels and patterns of autonomic, sympathetic, and parasympathetic activity. In a specific example, these techniques and configurations may be used to facilitate, expand access to, and improve a form of psychotherapy known as exposure therapy. Such exposure therapy may be provided, among other ways, together with and guided by techniques to monitor human organ functions during the presentation of audio-visual material. This process allows measurement and manipulation of the psychological state including cognitive states, vigilance states, arousal, interest level, desirability, appeal or revulsion, repulsion, or emotional valence or state associated with exposure to specific audiovisual materials. The process also allows for quantifying and cataloging of the psychological states and psychological state changes associated with audio-visual material over the time-course of its delivery. This quantification and cataloging of digital material by psychological state and induced state changes allows automatically selecting and presenting audio-visual content to induce desired psychological states and changes in these states, and using these methods in a variety of applications, including exposure therapies and related therapies in humans.

With the approaches discussed herein, typical and atypical functional responses to a sensory stimulus or sensory stimuli or sensory stimulation in exposure therapy can be used to select appropriate audio-visual content for the therapy, with the aim of inducing, reducing, increasing or decreasing anxiousness, stress or similar sympathetic-like psychological states over time. Such sensory stimulation may be deployed as part of a controlled and managed process, enabling a patient to achieve a desired level of appropriate balance between sympathetic and parasympathetic brain and peripheral responses after exposure time and repetition. The following thus discloses system, device, and method embodiments to monitor and to efficiently and automatically modulate the short term and longer-term balance of sympathetic and parasympathetic nervous system activity through exposure to a continuous stream of sensory stimulation delivered to an individual or individuals.

In various examples, stimulation could be provided from interactions with one or more individuals such a therapist or a group of individuals, whether in-person, or remotely. Existing forms of psychological assessment are performed by a clinician, based on the clinician's experience and a patient's subjective reporting of his or her mental status. The clinician can customize treatment techniques to the particular characteristics of the human subject or patient and the type of condition that is being treated. Effective delivery of psychological treatment depends on a clinician to design, deploy, review, and adjust therapy based upon the perceived amount of response by the patient to therapy. As a result, many approaches for psychological treatment have been limited to clinical settings with experienced clinicians, rendering therapies and treatment benefits inaccessible for many patients. Within the following discussion, clinician, therapist, psychotherapist, social worker, counselor, doctor, medical doctor, physician, psychologist psychiatrist, caregiver, or medical provider may be used interchangeably.

The acute, short- and longer-term impacts of the delivered stimulation, therapy or treatment, combined with the knowledge of how these impacts compare with a larger population of individuals, are monitored and adjusted in real-time to achieve a desired pattern and level of sympathetic and parasympathetic balance using physiologic responses as markers for this balance. Longer term impacts and the changes in these impacts over time (within a single delivery session and between repeated delivery sessions) can also be quantified, recorded and used to provide longer term summaries of changes in the responsiveness to the sensory stimulations that are automatically selected and delivered. Summaries of acute, short, and long term responses and responsivities will provide definitions of normal and dysfunctional sensitivities to stimulation in single or groups of patients and can be used in defining expected sensitivities to sensory stimulation, e.g. media content, for other applications. The techniques discussed herein may also be used together with one or more therapies that are optimally effective when delivered to a subject who is in a certain cognitive state prior to delivery of the therapy or therapies. Examples of such therapies include medication, psychotherapy, and brain stimulation techniques such as transcranial magnetic stimulation (TMS), deep TMS, transcranial direct stimulation, transcranial ultrasound, deep brain stimulation, cranial electrotherapy stimulation, electroconvulsive therapy, magnetic seizure therapy, and vagus nerve stimulation.

In one application of a disclosed process, a therapeutic goal or target psychological state is desired and induced to modulate the psychological state of an individual as a form of therapy (referred to herein as "exposure therapy"), which may be usable for anxiety disorders including general anxiety disorder, post-traumatic stress disorders, social anxiety disorder, obsessive-compulsive disorder, specific phobias, pain or chronic pain, panic disorder, or related conditions. In various examples, this exposure therapy delivery and feedback process may be implemented by use of a therapy selection system, optimization system, or therapy titration or dose ranging system, including in a computer implementation of such system.

As an overview of one relevant type of psychological disorder addressed by the present therapy selection system, anxiety disorders are common in adults and children. About 18% of United States adults and 25% of adolescents will experience anxiety according to the U.S. National Institute of Mental Health. 4% of adults and 6% of teens have severe anxiety. Often, people attempt to cope with anxiety by avoiding situations that make them feel anxious. This avoidance is, in fact, a learned inappropriate behavior that can make their anxiety worse (e.g. when they finally experience the situation or even as they imagine or anticipate the experience).

Individuals with general anxiety disorder often suffer from persistent worry. This worry can be about multiple concerns, including phobias (e.g. spiders, the physically disabled, vomit), death, finances, one's own heartbeat or similar internal (interoceptive) perceptions including pain, muscle stretch or fatigue, the future, etc. This anxiety may also be expressed in various irrational fears that something bad is going to happen. The results of such anxiety are excessive and difficult to control, and typically generate psychological and physical symptoms. Symptoms may include headaches, gastrointestinal symptoms, pain, chronic pain or back pain, insomnia, restlessness, irritability, muscle tension, and difficulty concentrating. In many cases these perceptions or anticipating or avoidance of these perceptions or the situations that they feel will be associated with inducing these perceptions, can be debilitating. It can lead to fear of leaving the house, fear of movement or exercise, fear of imagined or imaginal body perceptions including heart beat sensations, muscle pains, gastric or gastrointestinal sensations. These inappropriate fears and their association cause missed work or loneliness in adults, and missed school in children and may be associated with other conditions such as eating disorders, metabolic disorders, chronic pain conditions, or related conditions.

Treatment strategies used by mental health professionals vary for the current treatment of anxiety disorders. Medication is typically reserved for patients who have failed psychotherapy. Drugs include antidepressants, benzodiazepines, buspirone, pregabalin, or combinations of these medications. Overall effectiveness is gauged by patient reports, questionnaires or clinician observations of the patient during office visits. Ongoing or real-time measurement of responses using objective techniques are not available to measure brain or other central nervous system markers of the efficacy level or to confirm appropriate dosing or delivery of the treatment is achieved. Time to achieve behaviorally observed or subjective response takes several weeks, and not all patients respond to drug therapy. Other shortcomings of drugs include side effects, and a social stigma for needing to take drugs for a mental illness. In children and adolescents, pediatric psychiatrists will typically prescribe drugs for anxiety only after psychological approaches have failed.

Psychotherapy is commonly offered as a treatment for anxiety, and involves a patient working closely with a therapist to learn how to cope with anxiety conditions. Coping in this case can be controlled desensitization of internal physiological and neurophysiological process that are connected to the specific thoughts and experience in patients. Different approaches to therapy can vary in duration and frequency of contact between a patient and a therapist. Cognitive Behavior Therapy (CBT) is one prevalent form of psychotherapy that aims to help patients identify and manage factors that contribute to a patient's anxiety. The cognitive component of therapy can help patients understand how their thoughts contribute to their anxiety. The behavioral component involves repeatedly approaching situations that provoke anxiety so that patients can experience the lack of actual negative impact or harm that comes from the experience to learn that their feared outcomes are very unlikely to occur. Successive repeated experiences with exposure with demonstration of safe outcomes typically result in a reduction in sensitivity or responsiveness (stress or anxiety) over time. As an example, a patient may work closely with a therapist for many therapy sessions delivered over the course of several months to develop skills for coping with their anxiety.

Exposure therapy has developed as a form of cognitive behavioral therapy where the patient engages in a series of planned increasingly stressful contacts with an anxiety-provoking stimulus. An initial therapy session includes a clinician discussing and searching for specific phobia or anxiety provoking subjects or situations for a patient and working with the patient to determine the anxiety provoking subjects or situations and the relative anxiety each situation or subject may induce in the patient. Patients begin the session by confronting a moderately distressing or anxiety inducing stimulus. Each exposure session or exercise lasts until the anxiety level response has been achieved. Exposure to the stimulations that induce the desired anxiety level response is repeated within and over a series of sessions until it no longer causes significant distress or the induced distress is reduced to a desired state. The more intense the fear or anxiety signals, the greater the exposure time typically required before the anxiety response subsides. With exposure therapy, the number of sessions, durations of exposure, and repeated exposures per session can also vary, based on a therapist's direction.

With exposure therapy, once a patient has acclimated to an initially distressing stimulus, he or she gradually (e.g., over the course of weeks to months) works up to increasingly more distressing stimuli with lower or reduced levels of anxiety. A ladder or level of progression plan for that patient is established by the clinician. For example, the therapy treatment plan for a patient with a fear of spiders may be to initially look at a cartoon of a spider, then a photo of a spider from a distance, then a video of a spider crawling on a human arm, then a video of a spider on a face, then a video of many spiders crawling across a human face, and then to confront a real world stimulus (e.g. patient allows a live spider to crawl on his or her arm). Similar situations and procedures may take place for other fears including heights, airplanes, speaking in front of audiences, or other feared or anxiety inducing situations.

In many approaches of exposure therapy, after a patient's anxiety response subsides to each specific severity of exposure, the therapist would then lead the patient through a series of experiences that will induce an increase in severity or anxiety level of the therapeutic exposure, situation or content. Depending upon the response to the exposure the therapist may plan or change the plan of future exposures during the session. After the conclusion of a session, the therapist may also choose specific content for the patient to experience prior to their next therapy session based on how the patient tolerated the previously chosen content. For example, the size and number of spiders could increase over successive exposures, leading ultimately to videos of spiders crawling over someone's face. Over a series of sessions, the exposure anxiety provoking content would increase as a patient becomes less anxious or stressed by the series of exposures. The goal is to eventually decrease the patient's anxiety response to this stimulus.

Many approaches that have attempted to deliver exposure therapy have encountered a variety of limitations. First, therapists meet patients only weekly for 30-60 minutes and often begin by guessing at the type or amount of exposures that might induce an appropriate amount of anxiety in their patients. Clinicians assign homework exercises such as watching videos or performing challenging exercises. The compliance and outcomes from these homework experiences are not objectively monitored or documented. Clinicians currently rely upon subjective patient responses to describe anxiety levels, which may not be reliable. Every patient is different, and a patient's reactions may vary from one day to the next, so over time a patient may become more or less tolerant of a certain severity of exposure. Clinicians aim to provide enough of an anxiety-provoking stimulus to induce stress, but not so much that their patient becomes overwhelmed and prematurely discontinues their exposure session, or possibly even stops their remaining treatment sessions altogether. If a patient experiences overwhelming stress because exposure therapy progresses too quickly, patients may elect to avoid future exposure therapy sessions, which is a setback to treatment. If patient exposures progress too slowly, the course of exposure therapy becomes more prolonged than necessary. In the case of slow progression, patients may become discouraged by their slow progress and quit exposure therapy altogether.

Moreover, there are many more patients with anxiety disorders who would benefit from exposure therapy than there are qualified therapists who are adequately experienced and qualified to oversee the therapy. Therapists that are qualified may not offer the therapy due to the time needs to consider, plan, titrate, and deliver the therapy. Therapy delivery is also exacerbated by funding concerns, especially since many health care insurance policies do not cover mental health care. Coverage policies that do include coverage for mental health care may cap the total number of treatment sessions allowed, reducing or limiting effectiveness of the therapy. The logistics of seeing a therapist involves a number of challenges. Working adults need to take time off of work to attend to family obligations, and travel to the therapist's office. A parent who accompanies their child to therapy or who undergoes therapy is likely to miss work, while a child who undergoes therapy is likely to miss school. Moreover, the child may want to keep their weekly visits to the therapist confidential from classmates given the stigma of mental illness. Similar concerns may apply to adult patients. Although therapists may recommend real-world experiences or "homework" training sessions between formal sessions with the therapists, these informal sessions are not currently documented, quantified, adjusted from session to session or within a session based on the patient's setbacks or progress, or monitored.

Current methods of exposure therapy are inefficient, time consuming, and based upon a therapist's professional experience, training, and willingness to offer the therapy. Moreover, current methods are based on subjective assessments of anxiety states made by the patient or clinician. Current methods are not objective or quantitative. Therefore, current approaches to exposure therapy are difficult to titrate, deliver, monitor, or test. Stimulation experiences are not documented or precisely recorded—so transfer of best practices and improvements to the treatment are difficult. Outcomes to treatment of patient anxiety are not well documented or objective. Also current methods require subjective patient self-reports of their anxiety level to guide selection of exposures and to monitor outcomes—creating potential issues for patients who may not recognize subtle conscious or subconscious anxiety or who may be incapable of accurately describing their level of anxiety. Successful exposure therapy also may require periodic follow up or maintenance therapy to maintain the long-term positive outcome for the patient.

A shortage of trained clinicians who offer exposure therapy, has led to attempts to provide exposure therapies via new technology platforms. Such platforms have included the immersive presentation of content via virtual reality headsets, and delivery of content via the internet and mobile device applications. These approaches, however, are often not convenient for patients and do not deliver the exposure therapy based upon real-time physiology of specific patients. Additionally, with these approaches, there is currently no ability to objectively capture and document patient reactions in real time during the course of a single exposure therapy session, or over the course of multiple therapy sessions.

The present techniques and devices address these and other issues encountered with exposure therapy and other types of therapy that involve sensory stimuli to affect the autonomic nervous system and the brain regions which drive it. The following techniques provide the ability to induce distressing, stressful, or anxiety provoking situations based on real time, automatic, quantitative titration of exposure severity. Such exposure may be driven using selections of sensory stimuli, including new content which has not been reviewed, analyzed, or classified by the patient's clinician prior to exposing this content to his or her patient.

In various examples, discussed further below, sensory stimulation based therapies related to learning new and modifying existing psychological associations can be quantified and optimized in terms of the timing, intensity and pattern of the sensory stimulation to achieve a desired outcome or condition. For example, the therapeutic effect of exposure therapy and similar sensory stimulation methods will depend upon the duration, timing, pattern and intensity of sensory stimulations during a session. For some conditions or needs, a treatment regimen would alter intervals of sensory stimulation that induce a higher level of net sympathetic-parasympathetic drive or distress or anxiety with a recovery interval of sensory stimulation or no stimulation that allows or induces lower net sympathetic-parasympathetic drive or lower to no distress or anxiety.

In an example, sensory stimulation during the high distress interval can be titrated to reach or exceed a target level of sympathetic drive or net sympathetic-parasympathetic drive based on physiologic markers for a desired duration. For example, an individual with a baseline resting heart rate variability (HRV) score of 70 could receive sensory stimulation sufficient to reduce the HRV score to 50, measured at the peak of the distressing sensory stimulation or averaged or summarized over the desired duration of response.

In an example, sensory stimulation during the recovery interval can be paused or titrated to keep sympathetic drive or net sympathetic-parasympathetic drive at or below a ceiling level indicative of low or no distress. For example, an individual with a baseline resting HRV score of 70 could receive a pause in sensory stimulation during the recovery period or a level of sensory stimulation so that HRV remains above 60 for some duration or interval. A therapy session may consist of a number of alternating stimulation intervals to induce alternating periods of high and low net sympathetic-parasympathetic drive measured by sensed physiologic responses in real time. Alternatively, a measurement of the net total duration of sensory stimulated high distress intervals and recovery intervals can be measured and summarized over a treatment session or over a series of treatment sessions.

The duration of the higher distress interval may be from 250 milliseconds to 10 minutes, such as an interval of 30 seconds to 2 minutes. The duration of a subsequent recovery interval may be for 15 seconds to 20 minutes, such as an interval of 1 minute to 5 minutes. Specific interval parameters may be different for different desired outcomes or conditions. Specific sensory stimulation such as media scenes or music or spoken word or audiovisual material can be selected and delivered to fill the desired duration of each stimulation interval at the appropriate level of stimulation.

Each therapy session could begin with a warm-up period of 1 to 3 minutes where the level of distress induced by sensory stimulation is gradually increased until the target threshold of net sympathetic-parasympathetic drive or distress or anxiety for that session is reached, based on physiologic markers of net sympathetic-parasympathetic drive or distress or anxiety. Following a series of alternating target distress and recovery intervals, each therapy session could end with a cool down period of 2 to 5 minutes where the level of sensory stimulation is decreased to a level indicative of no distress. The overall duration and interval durations can be optimized for each patient or for different indications or outcome goals. Therapy sessions including a therapist or other therapy technique, or mode can utilize or synchronize therapist inputs or other therapies timed to occur at the appropriate time or time interval during the session or at a time period before or following the session.

Each therapy session could include a warmup period, a string of alternating high distress intervals and recovery intervals, and a cooldown period may last from 10 minutes to 120 minutes, such as from 15 minutes to 60 minutes. Treatment sessions could take place at a frequency of once or twice a day from one to 7 days per week, and could extend over 1 week to 2 years, such as from 2 weeks to 6 months.

Optimization of the sensory stimulation parameters such as duration or timing or valence or intensity of each interval in a series of intervals will influence the subject's neuroplasticity, impacting learning new and unlearning unwanted memories or psychological associations. Artificial intelligence or machine learning or other quantitative or statistical methods may be used to optimize these parameters for a particular individual using data from that individual, or data from other similar individuals.

These and similar types of interval based sensory stimulation could be optimized to produce superior clinical outcomes for specific conditions or therapy goals versus constant or continuous or unchanging levels of sensory stimulation that do not alternate or mix up the duration or timing or valence or intensity of the sensory stimulation. For other conditions or therapeutic goals, extended or shorter durations of intervals and session durations will allow improved quantification of therapy delivery and improved efficacy.

In further examples, the intervals of sensory stimulation or their parameters can be titrated and timed to occur at critical times or windows of an individual's receptivity to the sensory stimulation. This titration and timing to critical times or windows could optimize the impact of the sensory stimulation. Sensory stimulation can be titrated and timed to occur at specific points in biologic rhythms including circadian, diurnal, ultradian, or infradian rhythms. For example, sensory stimulation patterns could be delivered relative to sleep phase, sleep schedule, appetite, body temperature, hormone levels, alertness, blood pressure, or reaction times. Sensory stimulation patterns could be delivered relative to specific changes in body signals or changes that are measured with sensing, such as relative to electroencephalogram phase, brain or nerve signals, markers in blood or tissue fluids or gases, or relative to other sensed physiological signals at a specific phase or at specific phases of oscillations in sensed body signals to maximize the effectiveness of the desired outcome or for a specific disorder or unwanted condition.

Figure 1B:
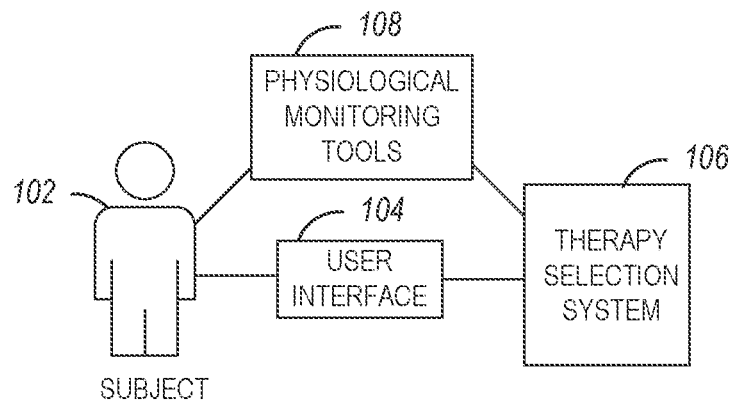

FIGS. 1A and 1B illustrate, by way of example, use case overviews of a therapy selection system. As shown in FIGS. 1A and 1B, a human subject 102 (e.g., patient) utilizes a user interface 104 in order to access and utilize the therapy selection system 106. The therapy selection system 106 provides relevant data outputs of exposure therapy content (e.g., photos, audio, video, etc.) via the user interface 104, as the therapy selection system 106 controls a progression and presentation of the exposure therapy content in a controlled manner. The therapy selection system 106 also obtains data from various physiological monitoring tools 108 (e.g., sensors, medical devices) used to monitor the subject.

In the example shown in FIG. 1A, a clinician 112 (e.g., therapist) also uses a user interface 110 in order to access and control the therapy selection system 106 if required. A clinician/therapist 112 may provide various data inputs on the type, severity, and condition of a particular psychological or behavior condition to be treated. The clinician/therapist 112 may also review statistics or data on the type and amount of therapy activities, the measured physiological responses to the therapy sessions, and overall patient reaction and responses to the treatment. Thus, various types of input and control may be offered via the therapy selection system 106 for clinician review, guidance, and consideration. In the example shown in FIG. 1B, a clinician is not immediately involved with the control or presentation of content from the therapy selection system. For instance, the scenario of FIG. 1B may occur in settings where the subject 102 directly interacts with a device (e.g., smartphone, tablet, laptop, video game system, etc.) providing computer-guided therapy in a closed-loop fashion, independently of clinician control or oversight.

In various examples, the therapy selection system 106 may be used to provide exposure therapy to relieve psychiatric related disorders including generalized anxiety disorder. In an example, a regimen of exposure therapy attempts to reduce anxiety levels through desensitization via successive and staged presentations of scenes to patients. Selection and presentation of appropriate audio, video, or audiovisual scenes or clips induces specific levels of physiologically quantified anxiety over time to achieve appropriate desensitization levels within and across therapy sessions coordinated or controlled by the therapy selection system 106.

Appropriate selection of scenes or clips is based upon desired anxiety levels as quantified by physiological responses to the scenes, such as those being captured by the physiological monitoring tools. Successive presentations of appropriate scenes to induce appropriate anxiety, while also not allowing or discouraging patients to engage in indirect or direct safety behaviors such as looking away from the scene, has been shown to reduce anxiety in patients over time through mechanisms such as desensitization, extinction, habituation, plasticity, and other changes in neurological and psychological responsiveness. Monitoring of therapeutic activities and patient states may be performed with the physiological monitoring tools using sensors in different forms, including but not limited to implanted devices, percutaneously inserted devices, minimally invasive devices, wearable devices, noninvasive devices such as handheld personal devices, or non-contact methods such as a camera or infrared sensor. Wearable devices may include a smart watch, fitness tracker, chest belt, smart bra or other clothing with sensors, disposable patches, tattoos, electrode tattoos, ear buds or headphones.

Figure 2:
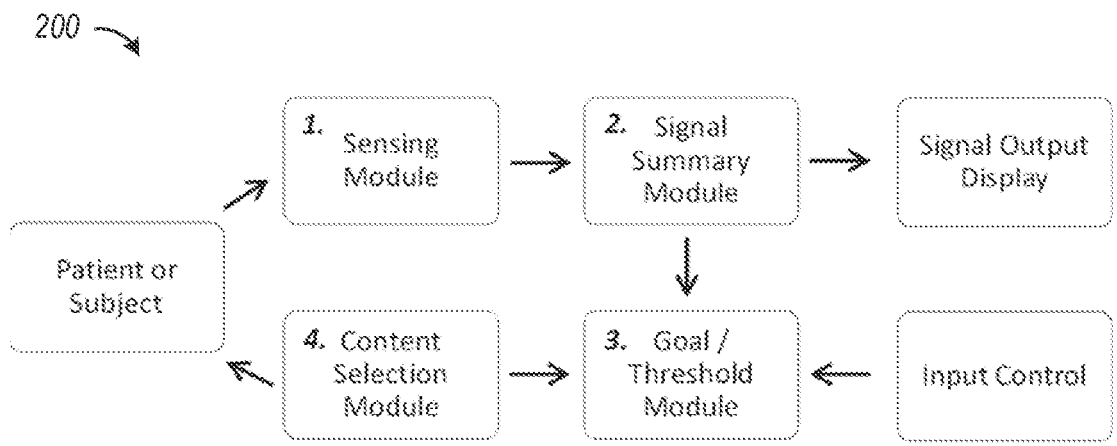
FIG. 2 illustrates a data flow among processing components of a therapy selection system, according to an example.

FIG. 2 illustrates a data flow among processing components of a therapy selection system 200 (e.g., an implementation of the system 106, discussed above). In the depicted implementation, the therapy selection system includes four components, although fewer or additional components may be used. Component (1) is a Sensing Module that captures and initially processes multiple physiological signals from a human subject (e.g., patient) during the delivery of therapy content. Component (2) is a signal summary module that provides additional processing and summarizations of signals including needed time courses, responses to successive repetitive or changing prior experiences (content or responses), signals relative to content, and the like. Component (3) is a goal or threshold module that compares the current summarized signal with the goal or reference signal (e.g. based upon user input as well as the overall ongoing therapy or experience goal) and provides a difference signal. Component (4) is a content selection module which automatically selects the next digital content from the content database, based upon the output from Component (3) and the available content database (including expected responses based upon prior uses of the content in patients and normal subjects).

In an exposure therapy setting, the processing functions of the therapy selection system will couple quantitative objective patient monitoring of physiological and behavioral responses during exposures to relevant sensory stimulation, with the automatic selection of the exposure content based upon the needs of the exposure therapy process. Relevant sensory stimulation exposures that are introduced, delivered, and controlled may include the following sensory stimulation (or other forms of sensory stimulation discussed herein): electrical, magnetic, electromagnetic, ultrasound, chemical, gustatory, taste, tastes, olfactory, smell, smells, tactile, touch, light touch, pressure, vibratory or other mechanical, temperature, thermal, air pressure pulses, auditory, hearing, sound, sounds, equilibrium, rotational equilibrium, gravity, gravitational equilibrium, motion, body position, proprioceptive, visual, lighting or other optical or visual or non-visual electromagnetic changes, music, images, photos, audiovisual media, video scenes or video clips, and startle inducing stimulations among other types of exposure content. Objective quantification of patient responses and anxiety state may be measured in real time by monitoring functions of the therapy selection system, including on a second-by-second or millisecond by millisecond basis. Such measurements may allow effective use of time during therapy sessions, while providing an objective basis for measuring therapy session progress and an objective means to assess overall therapy outcomes.

The monitoring process of the therapy selection system also enables transferable objective measurements of therapy success and improvement, transmission of evidence-based best practices and sharing of therapy materials and process among clinicians for research improvements as well as improved and transferable clinical outcomes. The objective selection and presentation of exposure content, coupled with the quantification of responses and therapy results, enable significant objective improvements of exposure therapies for a variety of disorders applicable to exposure therapy (including but not limited to anxiety, general anxiety disorder, social anxiety disorder, depression, obsessive-compulsive disorder (OCD), post-traumatic stress disorder (PTSD), and other psychological disorders).

Figure 3:
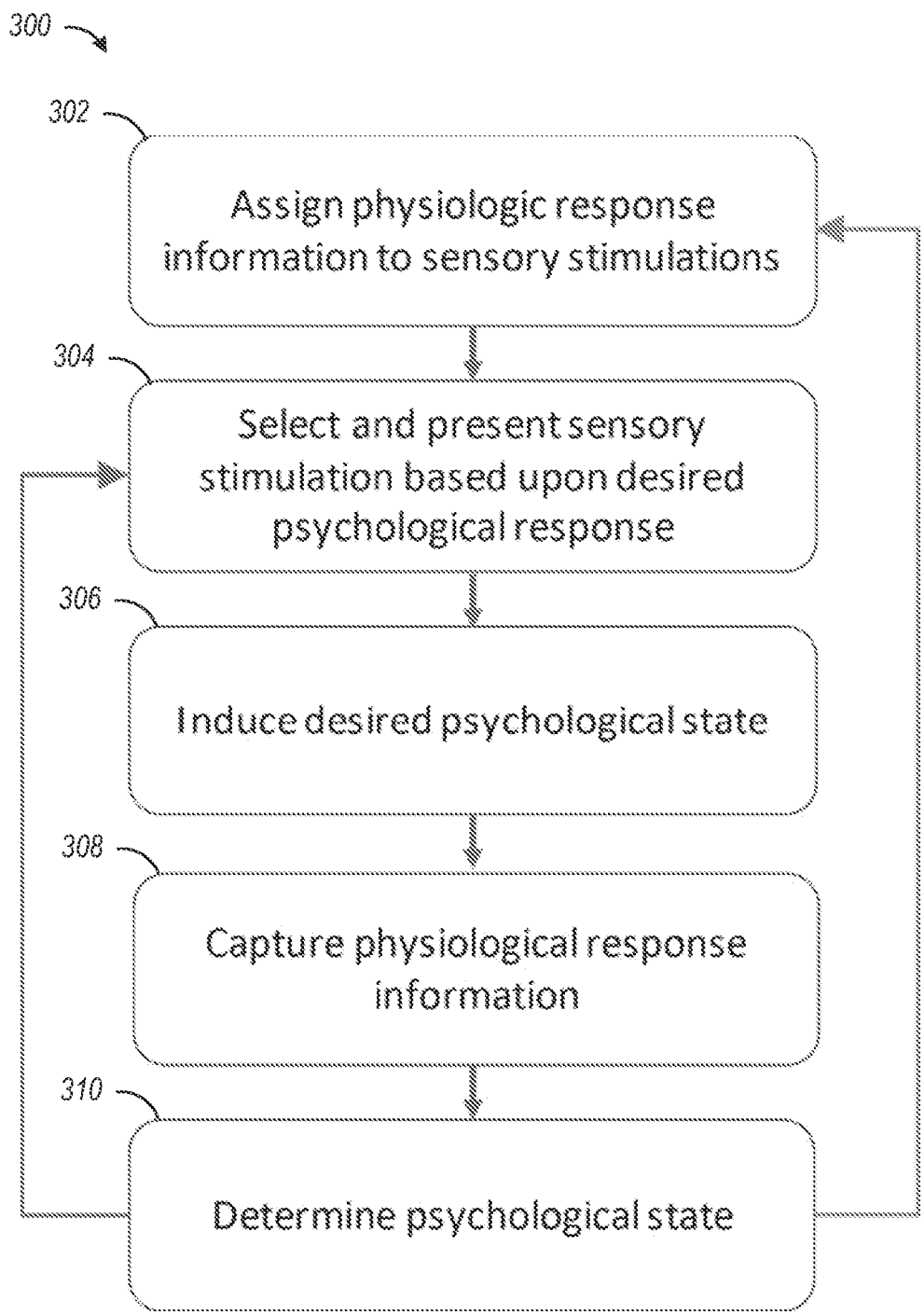
FIG. 3 is a flowchart of an operation flow used for performing therapy with a therapy selection system, according to an example.

FIG. 3 is a flowchart 300 of an example operation flow used for performing exposure therapy with a therapy selection system. It will be understood that the following operation flow is one example of usage for multimedia therapy content (specifically, involving the presentation of video, audiovisual, audio, or photo scenes) as part of an exposure therapy session. Other types of content and therapy types may follow this overall flow.

The operation flow of FIG. 3 begins with an operation (302) to assign physiologic response information to sensory stimulations, such as by developing or defining a correlation of physiological signals with emotional valence and intensity (V-I). This may be provided by a definition of V-I that offers an objective metric for measuring or quantifying these values at a particular point in time or time course or relevant to some content. Upon definition of V-I values, the use of such values may be integrated into the use of a framework that assigns or tags video or like multimedia content with relevant emotional V-I markers that define expected emotional responses in patients or groups of humans to the multimedia content. Further examples of the assignment of valence and intensity to media content are discussed with reference to FIGS. 12 to 17, below.

The operation flow of FIG. 3 continues with an operation (304) for the selection and presentation of sensory stimulation, based upon the desired psychological response. In an example, this involves the development and use of V-I tracking functions, to create, catalog, select, and deliver relevant content for exposure therapy. This may include the assignment of relevant physiological tags, based on a normal human response scale of valence and intensity, to a set of specific video scenes. This assignment is balanced by information which indicates how responses to valence and intensity measurements, of various media content, is altered in patients with anxiety or similar disorders. In various examples, this assignment and information may be recorded, retained, or refined as part of a trained predictive model (e.g., an artificial intelligence model) which learns common pathways for predicting responses to media content, with such predictions being trained to responses from normal humans or to the type of anxiety or other behavior disorder.

The operation flow of FIG. 3 continues with operations for the development and use of video processing functions, for the specific selection and use of specific scenes of content in exposure therapy settings. In an example, this sensory stimulation is presented to induce the desired psychological state (306), capture the physiological response information (308), and determine a resulting psychological state (310). The various physiological tags that are applied to media content may be used to select and present scenes, based on a desired outcome for therapy purposes. Specifically, such scenes may be selected and presented to induce a desired human response, in accordance with a therapy task or procedure. The resulting physiological signals from the human are then captured and used to control further output and operation of the therapy session. The resulting physiological signals may be used as feedback to modify the therapy session (or start a new session), or to provide model training, reinforcement, or modification.

Figure 4:
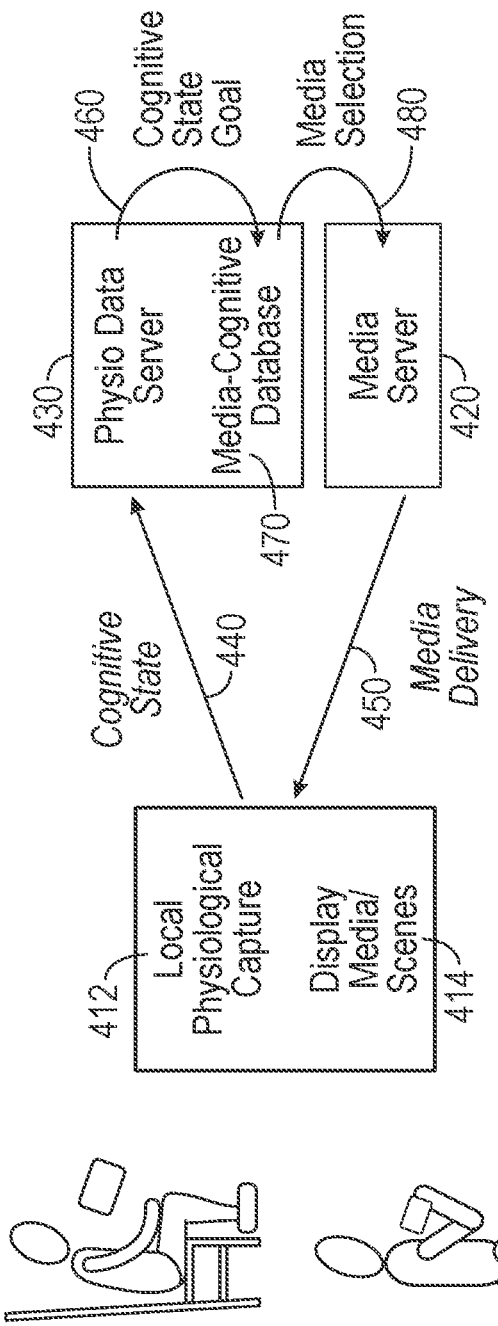
FIG. 4 is an illustration of a functional relationship between cognitive state and media delivery achieved with a therapy selection system, according to an example.

FIG. 4 is an illustration of an example functional relationship between cognitive state and media delivery achieved with a therapy selection system (e.g., system 106 or other system embodiments discussed above). The outputs

450 provided to the patient relate to the display of media content and scenes 414, provided from media delivery. The inputs 440 obtained from the patient relate to local physiological data and physiological data analyses, such as for physiological data 412 collected from patient sensors, questionnaires, and human-specified inputs. These inputs 440 are used to drive a measurement and monitoring of a cognitive state (a quantified cognitive state) of the patient.

The server-side functions of the therapy selection system may include: a physiological data server 430, which is able to extract and identify a cognitive state and cognitive goal progress 460 based on relevant physiological data measurements; a media cognitive categorization database 470, which stores information used to determine therapy goal states and progress, and measurements of media cognitive states to categorizations; and a media server 420, which uses the media cognitive information to fulfill a media selection process 480. Further discussion of the media selection and media rating processes are provided with reference to FIGS. 17 to 19, discussed below.

Figure 5:
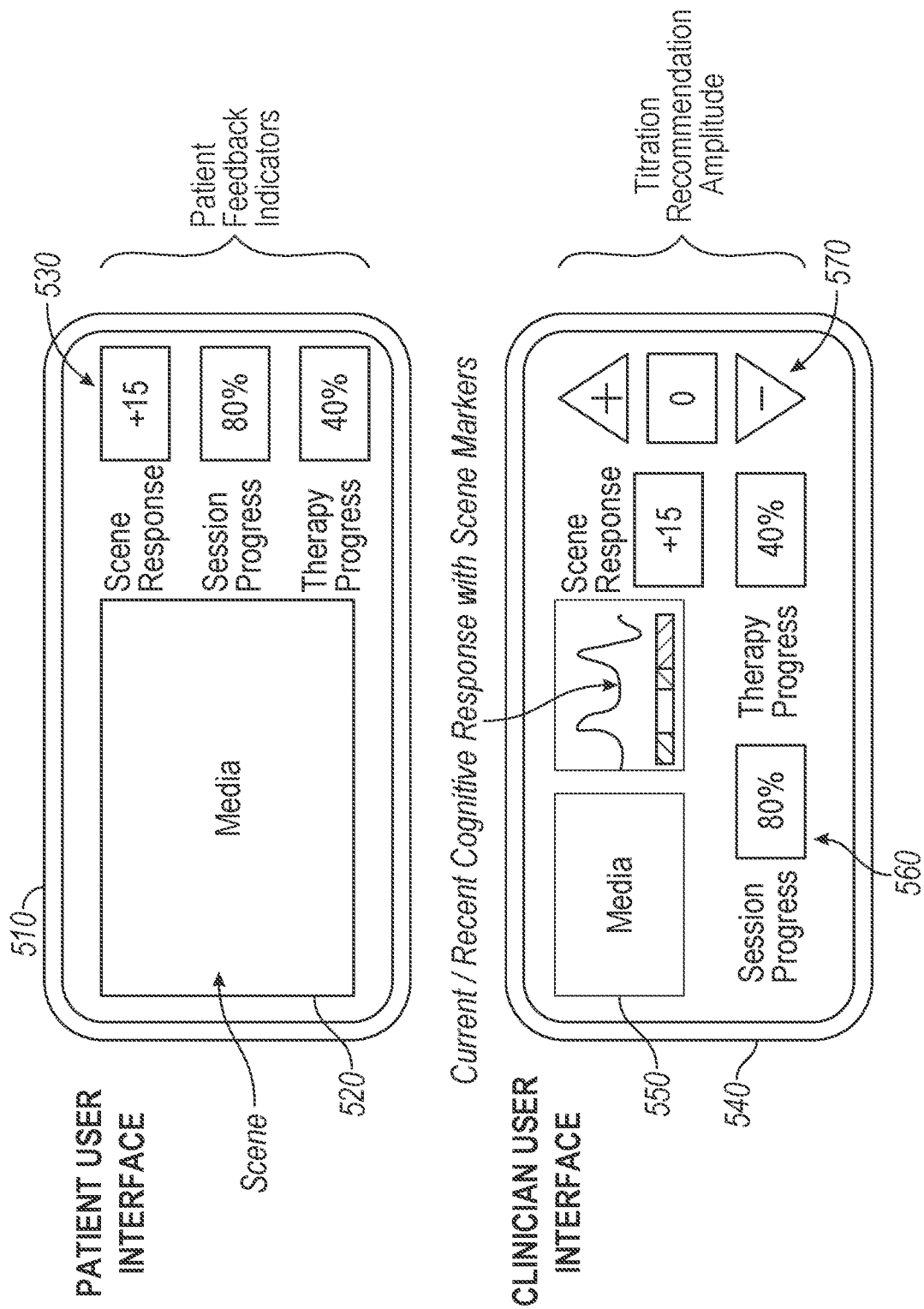
FIG. 5 is an illustration of patient and clinician user interfaces provided with a therapy selection system, according to an example.

FIG. 5 is an illustration of patient and clinician user interfaces provided with a therapy selection system (e.g., system 106 or other system embodiments discussed above), according to an example. In an example, a patient user interface 510 may include a media player area 520 which allows the output of a particular scene or clip (e.g., image, image sequence, video, etc.) for exposure therapy. The patient user interface 510 also includes a number of patient feedback indicators 530, which can receive and output relevant feedback information. Such indicators may include, an indication of a scene response (e.g., provided in real time from derived sensor data), an indication of a session progress (e.g., a measurement based on a session timeline or goal), or an indication of therapy progress (e.g., a measurement based on an overall therapy timeline or goal, made up of multiple sessions). Other types of feedback indicators may also be used.

Also in an example, the clinician user interface 540 may include a media player area 550 which previews or highlights the particular content to be output from a particular scene (e.g., image, video, etc.) for exposure therapy. The clinician user interface may include a number of inputs and outputs 560, 570 which allow for monitoring of a particular patient or patient therapy session progress. The relevant outputs may include a display of current or recent measurement of the subject's response or averaged response for a recent duration, session progress, and therapy progress, as provided in the patient user interface. Other outputs may include a graphical representation of a current or recent cognitive response, relative to scene markers or information tags associated with the scene and the expected reaction to the scene. Other inputs may include a control to allow the patient, a clinician or caregiver to make changes or recommend changes to a titration series or type or pattern of stimulation, The clinician user interface may provide its outputs in real time, such as for monitoring the patient exposure during an in-person therapy session. In other examples, the clinician user interface may provide its outputs for delayed playback or auditing, such as to see how a patient responded to a particular scene or series of scenes, session or series of sessions. The patient and clinician user interfaces may be designed to operate on separate devices, such as on respective tablets, smartphones, or workstations.

The use of the following monitoring and feedback scenarios via the therapy selection system may be conducted as part of a prescribed treatment schedule, such as specified by a clinician, or with an on-demand interface. For instance, an on-demand interface may enable patients to use this system on their own, with or without direct clinical supervision, to maintain or improve outcomes. Further, the present selection system may enable the comparison of patient and patient group progress to be quantified and compared.

Figure 6:
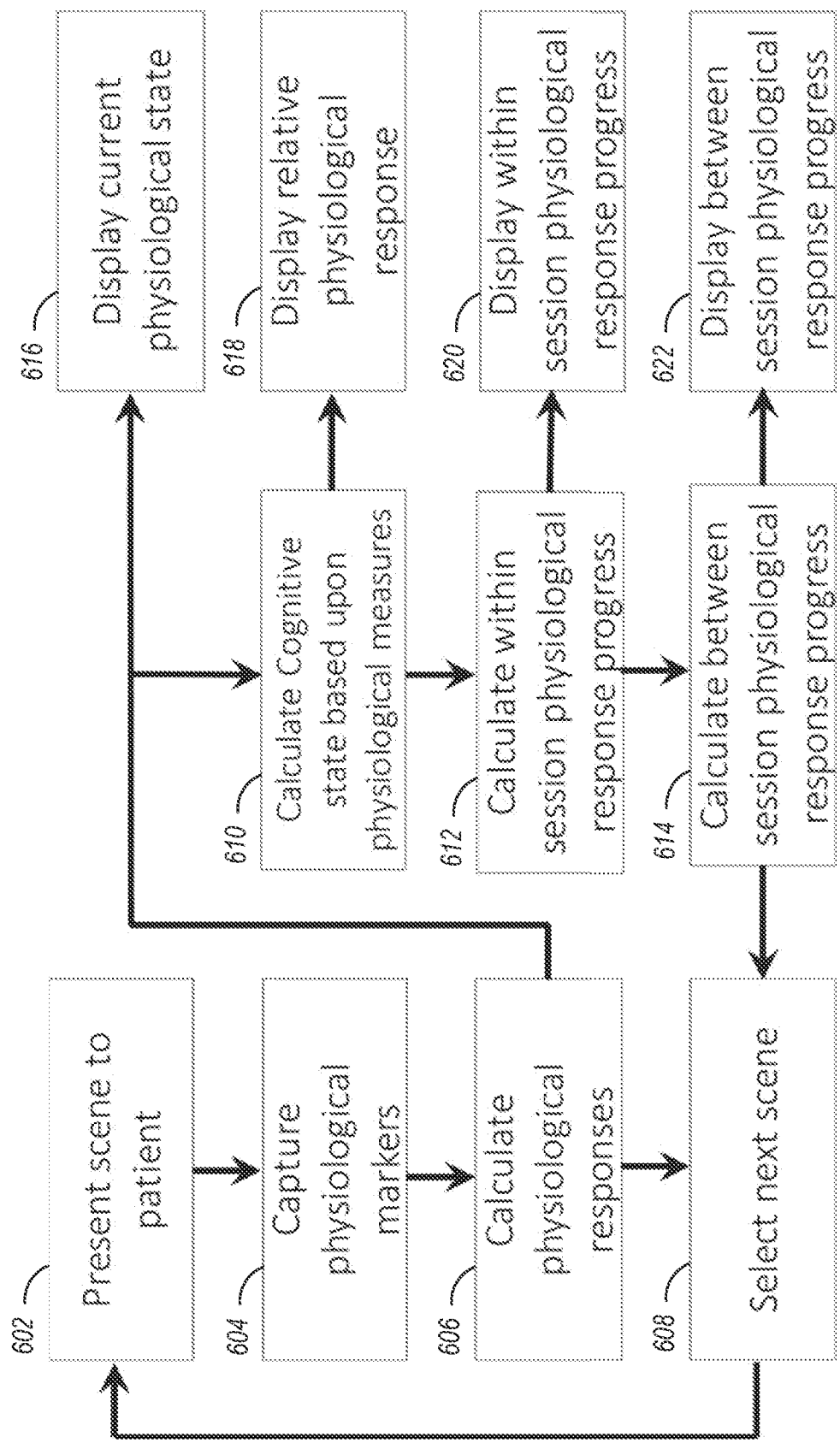
FIG. 6 is a flowchart of an operation flow for performing calculations and status displays with a therapy selection system, according to an example.

FIG. 6 is a flowchart of an example operation flow for performing calculations and status displays with a therapy selection system. The operation flow illustrates the types of outputs that may be presented during a therapy session via a user interface to the therapy selection system (e.g., with the patient user interface depicted in FIG. 5). Other types of user interfaces may also be used to facilitate the following operations.

The flowchart of FIG. 6 begins with the presentation (602) of a scene of exposure therapy content to the patient. During or after the presentation of the content, physiomarkers from the relevant physiological state of the patient are captured (604), such as with various types of sensor devices. These physiomarkers are then calculated into states or measurements of relevant physiological responses (606), and such states or measurements may be recorded and displayed (616). For instance, the physiological responses that are observed in real-time (during the playback of a scene) may be outputted and displayed during, or immediately after, playback of the media content.

The states or measurements of relevant physiological responses may also be correlated to other relevant information fields. In one example, the states or measurements may be used to calculate a particular cognitive state (610), based on the observed physiological responses. This cognitive state or a relative physiological response may be displayed (618) (e.g., in the patient user interface) during, or immediately after, playback of the media content. In another example, the states or measurements may be used to calculate a particular physiological response progress (612) within a session. This response progress may be displayed (620) (e.g., in the patient user interface) during, or immediately after, playback of the media content. In yet another example, the states or measurements may be used to calculate physiological response progress (614) between sessions, scenes, or other observations. This response progress may be displayed (622) (e.g., in the patient user interface) during, or immediately after, playback of the media content.

Based on the relevant physiological responses, and in some examples based on the physiological response progress occurring between sessions, new scenes may be selected (608) for presentation to a patient. Additional rules or constraints, profile information, and results of clinician feedback may also be involved to change the type and content for presentation.

For specific use of digital content, delivered to a patient in a cognitive behavior treatment process, it is important to monitor the times of signal acquisition relative to presented digital content. Physiological stress responses will be induced and quantified for durations of seconds to minutes and over durations of up to hours. Continuous presentation of stress-inducing segments will typically cause diminished responses as a patient's cognitive and sympathetic systems habituate or adapt to ongoing sensory stimulation. Specific segments of content may be associated with intense but short-term responses such as brief startle or surprise. Ongoing or maintained or repeated delivery of these segments will typically not induce similarly large responses but more subdued responses or even no response. Likewise presentation of different content or less startling content may renew the startle response. The time course for the recovery from a prior response or the renewal of the responsiveness following a prior stimulation or response may be patient or condition specific. Therefore it is important that any therapy use of digital content reflect the expected and prior delivery of content, the time courses for content and responsiveness changes, prior content delivered and even the longer term (weeks or months) of content delivered and responses measured from an individual or populations. Large databases and physiological responses of the populations that view them will provide essential data for specific uses in exposure therapy or other potential therapeutic or non-therapeutic uses. Individuals may also self-report what they felt when viewing specific content with a recommendation rating on a variety of aspects of the audiovisual content such as quality of the video sound, quality of the video imagery, relevance to their condition, to what extent it was boring or interesting, to what extent it induced feelings of anxiety, to what extent they believe it helped them, to what extent they recommend other subjects with a similar diagnosis and severity or sensitivity level view this content. Recommendations could be in quantitative (for example zero to five stars), or in the form of written comments. System would allow users to see the other videos that patients like them with the same diagnosis severity level used in their exposure therapy and in what sequence and time course they were viewed.

In further examples, these techniques may be integrated in a system or device used for monitoring or diagnostic purposes. The system could be used as a regular screening tool to assess the emotional sensitivity of large numbers of subjects to a variety of audiovisual content, as in regular screening of students in elementary, middle school, high school, and college, adults who currently work or previously worked in professions known to be high risk for anxiety disorders such as the military, and as part of regular health maintenance screenings by pediatricians, primary care physicians, and large population based health providers such as the Veterans' Administration, and payors such as Medicare (CMS), Medicaid, or private insurance companies. It could be used to help a clinician who is getting to know a new patient to understand the patient's sensitivity to a variety of exposures. It could be used intermittently, for example every day or week or month or year to assess how a patient is doing either during or after a series of therapy sessions. If the patient's anxiety seems to be increasing or returning, the patient and clinician would be notified that it may make sense to reestablish exposure therapy to prevent the worsening of a patient's anxiety, or refresh or relearn technique to manage anxiety.

For subjects who have completed a course of Exposure Therapy, device could be used regularly as a maintenance therapy to allow patients to preserve their gains from exposure therapy and avoid relapse. Regular exposures to anxiety inducing triggers, especially triggers that a patient rarely encounters, could be used as a reminder to patients that anxiety sensations will pass.

With the present examples of exposure therapy, the therapy selection system measures, selects and delivers digital content based upon the acute (real-time) physiological signals acquired as well as measurements over durations of milliseconds, seconds, minutes, hours, days weeks and months. For specific content segments, the typical responses in normal and anxious humans will be monitored for anxiety signals. Successive repeated delivery will be used to characterize and monitor the time course of responses and desensitization or sensitization of the responses following prior content delivery.

Time courses for re-sensitization following non-stimulated or other stimulations also may be monitored with the therapy selection system. Short term time courses (ms to s), medium term (s to minutes and hours) and long term (hours to days and weeks) may each be measured. Reference knowledge of these time courses will be captured for normal and anxiety subjects. Comparison of actual responses in an individual will be made to these references to select subsequent content for delivery. The goal for the selection and delivery of content will be to strike a balance between the possible over stimulation of a patient, which may cause them to discontinue therapy, and under-stimulation which would lengthen the duration of therapy time or limit therapy effectiveness. For reduction in anxiety as a therapy, the goal will be to reduce the anxiety response to single, short term exposure, series of delivered exposures within a session and multiple sessions of exposure. These sessions may also be followed by ongoing maintenance sessions that continue exposure, to increase the effectiveness of the overall treatment results.

FIG. 7 is a flowchart of an example measurement and evaluation operation flow for presenting scenes, as part of a therapy session, using the present therapy selection system (e.g., the systems discussed above). Such measurements may be integrated into the measurement and scene selection operations (710) depicted, for instance, in FIGS. 3 and 6. As shown in the following flowchart, such measurements may allow the evaluation of physiological response targets for individual scene presentations or for an overall therapy session (which consists of multiple scene presentations).

The flowchart of FIG. 7 begins with the measurement of signals (702) at a first point in time, followed by the selection (704) and presentation (706) of a scene for therapy purposes. A measurement of the signals (708) at a second point in time then occurs. If physiological targets are not reached (712), as indicated by the second measurement, then the scene is continued or replayed, or another scene is selected and presented. If physiological targets are reached (712), as indicated by the second measurement, then an evaluation is performed (714) based on whether the physiological targets for the session are reached. If the physiological targets are not reached for the session, then another scene is selected; if the physiological targets are reached for the session, then the session may conclude.

Thus, during exposures to specific scenes, the physiological state (determined by physiological signals) can be captured and used as a measure of progress, to determine if the ongoing exposure therapy session has appropriately reached or moved the limits of patient tolerance. Based upon progress of a specific scene or the overall session, relative to the physiological state, a new scene can be chosen. Or if the session progress has been achieved, the session result can be quantified and ended.

FIG. 8 is a flowchart of an example operation flow for evaluating scene presentation based on a physiological response. The flowchart of FIG. 8 specifically illustrates how a physiological target may be analyzed for a scene, based on multiple scene-related outcomes. This analysis may include, the measurement of a physiological response measurement (802) between the second measurement and the first measurement, followed by a series of evaluations relative to scene targets. The evaluations may include, a first evaluation (804) based on whether a peak physiological response magnitude for a scene is met or exceeded; a second evaluation (806) based on whether a physiological response target reduction in anxiety over time also referred to as decay for a scene is met or exceeded; and a third evaluation (808) based on whether response target totals for a scene is met or exceeded. If any of these are not met or exceeded, then the determination for the scene may be indicated as negative.

In an example, objective correlates of subjective states may be determined using measurement techniques for physiological responses. Several signals can be captured and summarized for inclusion in an overall measure of patient anxiety state. For instance, the scaled response score used to assess the change in anxiety level and emotional distress will be correlated with a measurement of subjective units of distress, described on a scale, such as the SUDS (Subjective Units of Distress Scale). SUDS represents a clinically used, scaled description of anxiety level between a scale of 0 to 10 (or 0 to 100) for measuring the subjective intensity of disturbance or distress experienced by an individual. SUDS is currently used in some forms of exposure therapy as a measure of patient state. SUDS is often assessed by simply asking the patient to rate a level of anxiety on a numerical score or having them document it in a journal. The present systems and techniques provide an objective metric to replace a clinician's subjective assessment of a patient's anxiety, or a patient's subjective self-reported value like SUDS.

As is understood, a SUDS value or similar scaled response score may provide a subjective indicator to quantify a patient psychological state, such as used with anxiety therapy to identify the level of anxiety induced by exposure to a specific stimulus or stimuli that may induce anxiety or distress in a patient. A measurement of SUDS may be used to screen for and contrast, for example, among specific situations, objects, or experiences that induce anxiety or distress in a patient to identify those situations, objects, or experiences along a hierarchy of experiences. The measurement is also used within an anxiety condition such as a fear of spiders to understand the level of anxiety induced by different traits or types of spiders, how the size of the spider may increase or decrease the amount of anxiety, whether other triggers associated with spiders are distressing or problematic, and the like. The measurement and use of SUDS or a similar scaled response score describing psychological state may be integrated with workflows and analysis provided by the present systems and techniques. For instance, a patient may define a SUDS criteria, while setting up a therapy, to help control how the treatment might be delivered.

Within the present systems and techniques, an objective measurement of stress such as a scaled response score (e.g., relative to a goal response score) would be used like SUDS to help track how distressed a patient is during exposure therapy, and serve as a measurement of the effectiveness of exposure therapy (e.g., whether the score goes down over time). Objective tracking of stress or anxiety or distress level may be accompanied by other evaluations of patient inputs (e.g., patient inquiries, questionnaires, SUDS). For instance, a patient might be asked to indicate his or her level of distress using SUDS over the course of an exposure intended to invoke a range of stress reactions, from low distress to high distress. This use of SUDS or scaled response score may help identify correlations to potential objective physiologic metrics, or used as part of a machine learning process to develop an objective, physiologically based assessment of stress level in the patient. The present techniques thus provide a feedback loop using objective, physiologic measurements of psychological state to help facilitate a measurement and treatments with objectivity, speed, and efficiency.

It will be understood that objective and subjective responses of an individual to content may show higher or lower reactivities or sensitivities to media content relative to normal human population. These responsiveness differences are associated with dysfunctions such as anxiety, depression, phobias, pain, or other disorders. Changes in this responsiveness over time will show effects of stimulation or time-linked changes in the severity of the disorder—or even normal changes in responsiveness (e.g. relation to time of day, fatigue, distractions, emotional states, comorbidities, or medication use). The presently described therapy selection system can sense a subtype of anxiety disorder and establish therapeutic plans to be optimized for respective subtypes of anxiety or other disorders. The system can also sense a change in a disorder or severity of disorder, and modify a therapy approach during a session or across multiple sessions over the course of therapy.

Figure 9:
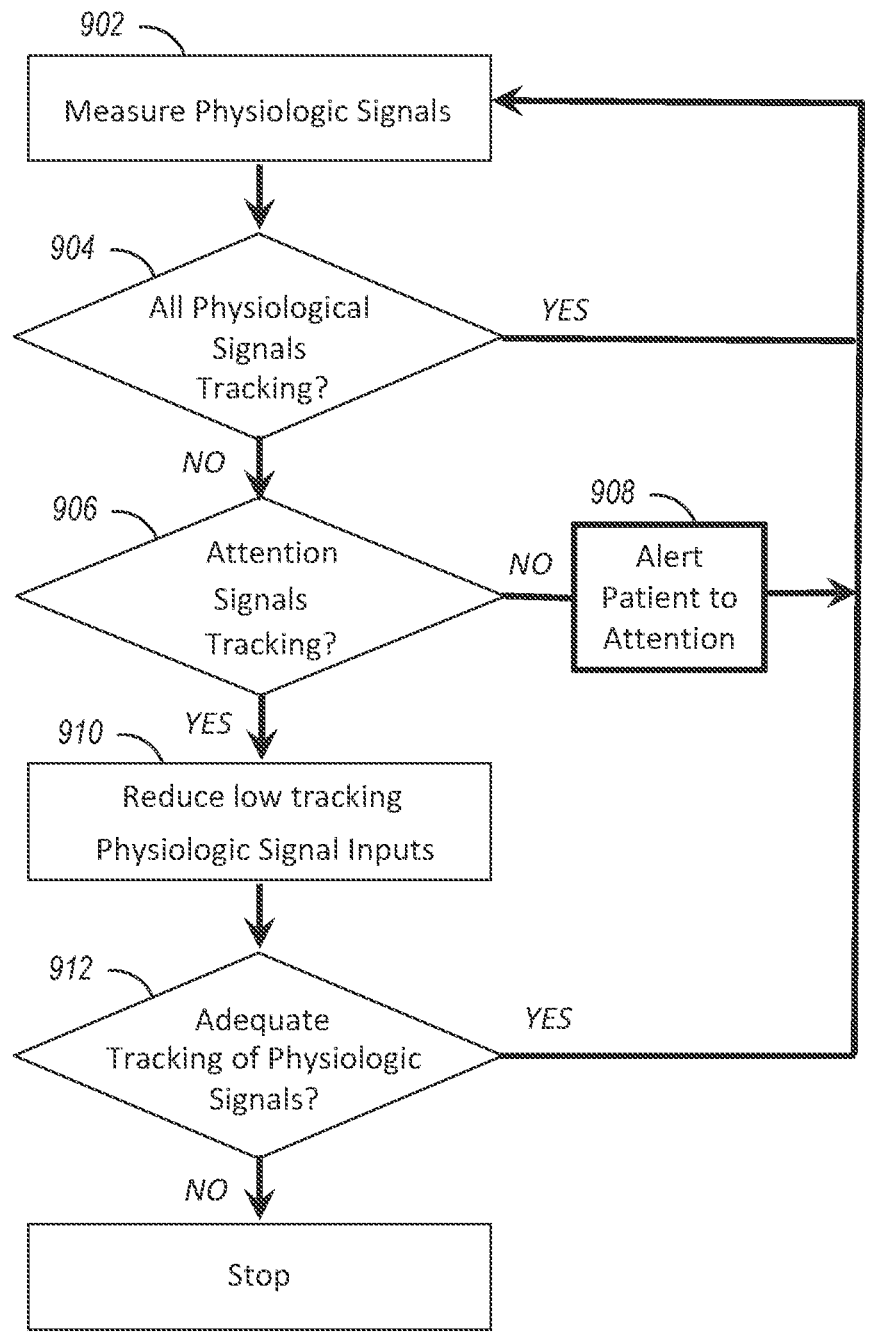
FIG. 9 is a flowchart of an example operation flow for evaluating signal tracking based on a physiological response, according to an example.

FIG. 9 is a flowchart of an example operation flow for evaluating signal tracking based on a physiological response. The flowchart of FIG. 9 specifically illustrates the use of a signal concordance module in a therapy selection system (e.g., system 106), showing how a measurement of multiple physiological signals (902)—such as multiple signals or data values from multiple sensors—may be evaluated and considered. In an example, an activity monitor may be incorporated in the device to allow software to disregard changes in physiologic response that are likely caused by activity rather than the audiovisual stimulus. Activity monitors may include an accelerometer, gyroscope, GPS, light sensor, or EMG sensor. The evaluation of the physiological signals may include performing attention tracking (906), an evaluation of an agreement of physiological signals within a patient (904), and evaluation of a predicted agreement of signals within a patient to those predicted (912) based upon prior viewing of media by other patients. If attention tracking is not properly occurring, then the patient may be alerted (908); additionally, even if attention tracking is occurring, low tracking physiologic signal inputs may be reduced or disregarded (910).

Attention tracking may be used as a physiologic response signal, allowing for adjustment of the media content valence or intensity to either less or more distressful content based on a subject's attention. For example, a subject may consciously or subconsciously look away from a media screen as a fear avoidance response if a media scene induces an overwhelming level of distress. Fear avoidance as the cause for looking away could be confirmed by other physiologic response signals that are markers of distress. In that event, media content believed to induce less distress may be displayed that a subject could view without the urge to look away. Likewise, attention tracking may also be used as a physiologic response signal to identify a target maximum level of distress to be induced by media content. Media content of increasing distress could be titrated to establish the level of content distress that causes the subject to look away; subsequent content could then be selected so that the subject would tolerate viewing the content without looking away. Attention tracking may be used to encourage compliance with viewing media content; should subject become less attentive for reasons other than fear avoidance as determined by certain physiologic response signals which serve as markers of loss of attention, an alert such as a sound or vibration or image could notify the subject so that subject resumes paying attention to the content. Attention tracking may also be used to determine the veracity of other physiologic response signals; for example, if a subject is not paying attention to the media content then the other physiologic response signals would viewed in light of this reduced attention until the subject's attention to the media content has been restored.

Attention tracking can utilize inputs such as eye tracking, eye movements or gaze location directed to media screen, lateral eye movements, eye shape, pupil diameter, iris size, heart rate changes, heart rate variability changes, respiration rate and pattern, skin potentials and conductance changes, blink flurries, miniblinks, blink rate and amplitude and duration, declines in eye movement and pattern, EMG, EEG signals of attention and vigilance (including evoked potentials, coherence and activities in specific EEG bands such as increased slow wave frequency EEG activity, amplitude of event related EEG potentials, attenuation of awake EEG frequencies (e.g. alpha waves), increase in theta waves, or decrease in beta waves, responsiveness of light flashes (Oxford sleep resistance test), reaction time, attention tracking continuously, and the like), including the acute signals, means, and variability of these measured signals to ensure the subject is maintaining vigilance and attention directed to the media being presented.

The concordance or agreement of physiological markers within a subject is measured during the presentation of digital media. The series of physiological markers will include multiple markers that are expected and found to track in agreement or with specific timing or known temporal characteristics between them and the presented stimulation. Loss of some markers or altered timing of signals will be sensed by the system as loss of concordance of one or more signals. If there is a loss of agreement or concordance the system will ensure the attention signals are tracking through signals and relationships between signals remaining or more appropriate for concordance tracking and confirmation. If attention signals are tracking the system will reduce weighting reliance on the non-concordant signals and continue monitoring. If attention tracking signals reveal that the subject attention is not focused upon the digital material adequately the system will signal loss of monitoring ability.

Tracking may be performed based on agreement between physiological signals and comparison population data from normal subjects and patients. Responses to specific scenes that induce large distress or anxiety responses in specific patients or across the population are most useful for assessing concordance. If all signals are tracking in concordance, then the use of the physiological signals may continue normally. If concordance of the physiological signals is reduced or lost, while the attention signals continue to track (i.e. subject is paying attention to the exposure), then additional processing may be performed to reduce the low tracking inputs. This additional processing may include evaluating whether adequate tracking is occurring among remaining inputs. If adequate tracking concordance is occurring, then the measurements may continue; if adequate concordance is not occurring, then signal measurements may be stopped or the relative weighting of signal inputs can be adjusted to allow increased weighting to be focused upon the remaining concordant signals. If a threshold number of signals lose concordance the signal capture can be discontinued or an alert could indicate loss of concordance. With this use of signal concordance tracking, multiple signals may be measured and considered, even in settings where signals or measurements are irregular. Reducing or eliminating dependence on any particular type of sensor allows continued use of the remaining measures or stopping the process if a sensor reading becomes unavailable. Feedback to the subject or caregiver or similar monitor or system can alert the user that more vigilance or attention is possible. The sensing system can then sense for improvement and maintenance of appropriate concordance for a session. The concordance data and responses to alerting can be used in cataloging the video or sensory stimulation series.

While presenting scenes and clips from the present therapy selection system, patients and subjects can be monitored using multiple measurement systems to quantify physiological measures of anxiety, psychological stress and state of autonomic activation (relative sympathetic and parasympathetic state). Measurements can include variables or physio-markers including heart rate, heart rate variability including high and low frequency components and respiratory sinus arrhythmia, respiration rate and pattern including regularity, depth, frequency, and increases and decreases in these measures over time including abrupt gasps or similar changes in breathing pattern, electromyography (EMG) of musculature including facial, cranial, neck, torso and limb as well as axial musculature, postural changes, accelerometer, or video based measurements of body, eyes and pupillary response and eye/periorbital musculature activities, galvanic skin conductance and potential measurement, eye blink startle response induced, eye blink rate and intensity and duration, EEG, head movements, blood flow skin perfusion and changes, pilomotor reflex and erection or goosebumps, body movements, lurching or jumping, body sway changes, shivering, trembling and other changes in movement pattern, freezing of movement or similar changes in posture or movement, muscle stiffness bradykinetic, baroreceptor, blood pressure and vascular tone markers, facial expression, eye widening, mouth changes, reduction in exploratory behaviors, changes in speech patterns including trembling.

As suggested above, multiple physiologic markers can be tracked for concordance. For example if content expected to induce a large physiological response causes no or lower response than expected then concordance between signals can be used to ensure that the patient is attentive to the content (e.g. eye tracking). Likewise if content induces high responses then signals (such as activity or motion) can be checked to ensure that the patient is not engaging in significant levels of activity such as physical or other activity that may impact the measurement of cognitive response or anxiety. The exposure session can be paused until the patient's attention resumes or the patient's activity such as physical or other activity levels are reduced to once again allow sensing of signals.

Tracking multiple physiologic markers in parallel will also allow the system to ignore a specific marker or specific markers that do not seem to track other physiologic markers or expected physiologic responses, until concordance is reestablished. Measurement error, sensor dysfunction, environmental factors such as temperature or humidity or lighting or noise, or external factors may cause inaccurate readings of a subset of sensors. Internal factors such as hydration status, medication use, anatomical differences, or pathophysiology may cause inaccurate or discordant readings of one or more sensors.

A non-exclusive list of physiomarkers used for measuring a physiologic state, may include:

Galvanic skin response, galvanic skin resistance, galvanic skin potential, skin conductance, skin conductance response, electrodermal response, skin temperature EEG signals and bands, resting frontal activity, delta, alpha, beta, theta, gamma or alpha-theta brain EEG ranges or their relationships.

Sympathetic nerve activity, micro-neurography, Blood pressure, systolic blood pressure, diastolic blood pressure Pulse blood pressure, pulse pressure, blood volume pulse, pulse transit time Blood pressure shape, waveform or pattern Baroreceptor response and sensitivity Heart rate, heart rate variability, low frequency heart rate variability spectral power, high frequency heart rate variability spectral power, ratio of low to high frequency power Pupil diameter, pupil dilation or constriction responses, accelerometer or video based measurements of body, eyes and pupillary response and eye or periorbital musculature activities Pupillary reflex response, startle response, startle reflex, eye blink induced by startle, eye blink rate or intensity or duration Eye movement/extraocular muscle activities Eye movement and tracking—to monitor fixation location and micro movements such as saccades Respiratory rate, respiratory pattern including regularity, depth, frequency, and increases and decreases in these measures over time including abrupt gasps or similar changes in breathing pattern Respiratory sinus arrhythmia Startle reflex, Blink startle response intensity, duration, induced startle response and other startle responses Peripheral blood flow and changes Arterial wall stiffness, vascular elasticity, pulse wave velocity Facial expression using imaging or EMG (e.g., corrugator supercilii muscle)

Blood composition including immunological and metabolic markers (e.g., glucose, catecholamines, epinephrine, norepinephrine, markers of DNA damage, stress hormones, corticotrophin releasing hormone, adrenocorticotropin hormone, cortisol, bound cortisol, free cortisol, glucocorticoid, interleukins, cytokines, C-reactive protein, chemical markers of inflammation and immunological markers and state including leukocyte number and composition, lymphocyte number and composition, neutrophil number and composition,))

Tumor necrosis factor-alpha (TNFα) measurements

Saliva or urine composition and markers (e.g., cortisol, catecholamines, epinephrine, norepinephrine)

Sleep disturbances and changes

Blushing and facial or skin or superficial blood flow

Movement such as head or neck or other body movements, shaking or trembling hands or forearms—measured by use of EMG, mechanomyography (MMG) or imaging or accelerometer-based methods or similar motion capture methods Speech patterns such as halting, quivering speech pattern, pitch, or enunciation These physiological measurements can be captured in patients or subjects while viewing or experiencing a scene or clip. Measurements can be captured and quantified relative to the time-synchronized scene, clips or experiences that are presented to the patient or subject. Relative changes in the measurements can be quantified for subsequent presentations of anxiety inducing as well as non-anxiety inducing agents. Algorithms to weigh and quantify relative autonomic or anxiety quantification can be used.

Figures 10, 11:
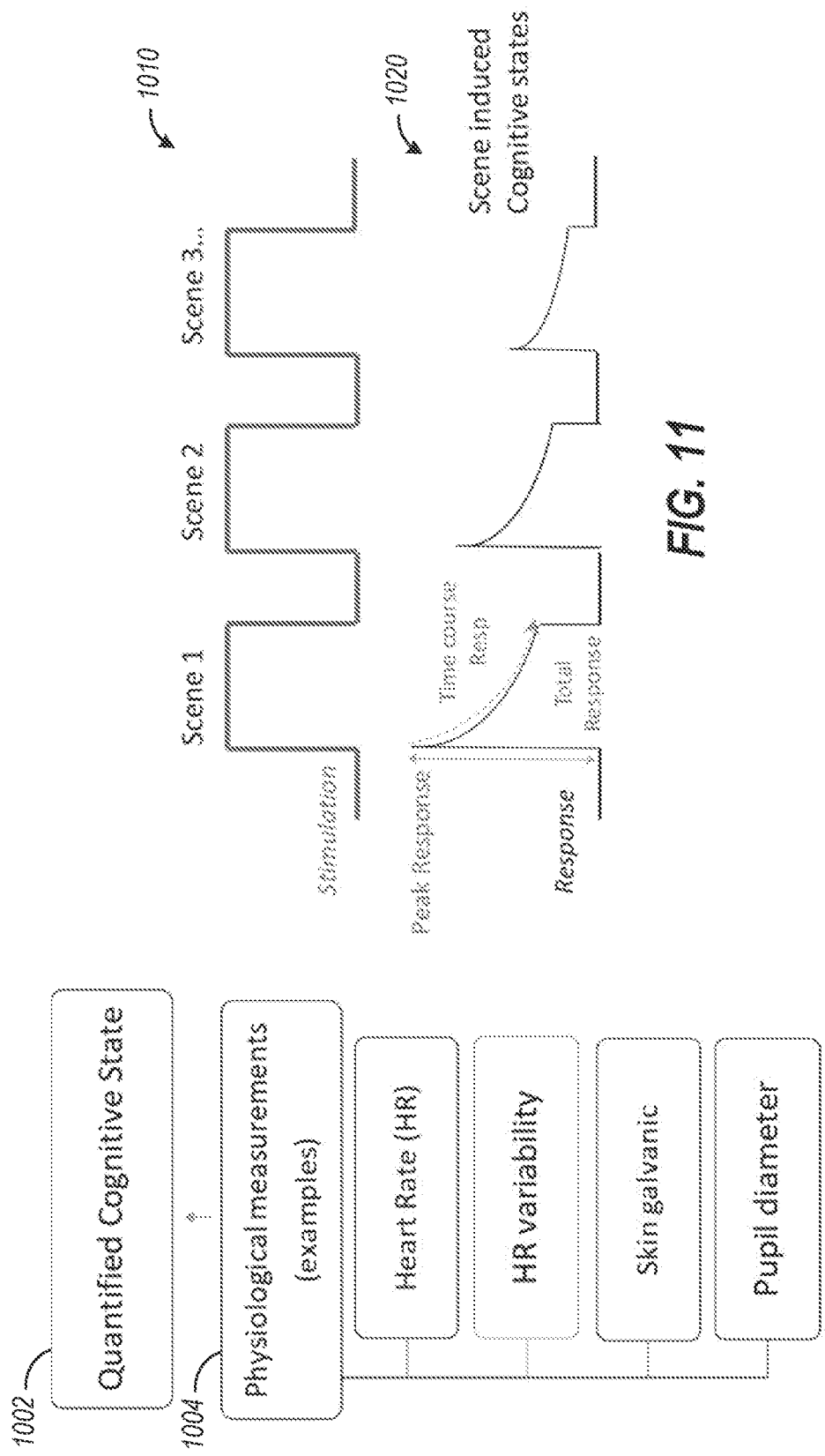
FIGS. 10 and 11 illustrate a data listing and charting of cognitive state information, respectively, according to an example.

FIGS. 10 and 11 illustrates an example data listing and charting of cognitive state information, respectively. The data listing of FIG. 10 shows how example physiological measurements 1004, such as heart rate, heart rate variability, skin galvanic response, startle response and pupil diameter may be collected and associated with a quantified cognitive state 1002. The charting of FIG. 11 illustrates how various physiological responses 1020—and scene-induced cognitive states 1010—change relative to the presentation of respective media content scenes. Notably, responses are dependent upon the number, sequence, duration, intensity, variation, valence, pauses, patterns, and content of stimulation that is presented—both within and across scenes. Such responses that are experienced by the patient may indicate adaptive response characteristics to the exposure, such as adaptation, desensitization, accommodation, etc.

Figures 12, 13:
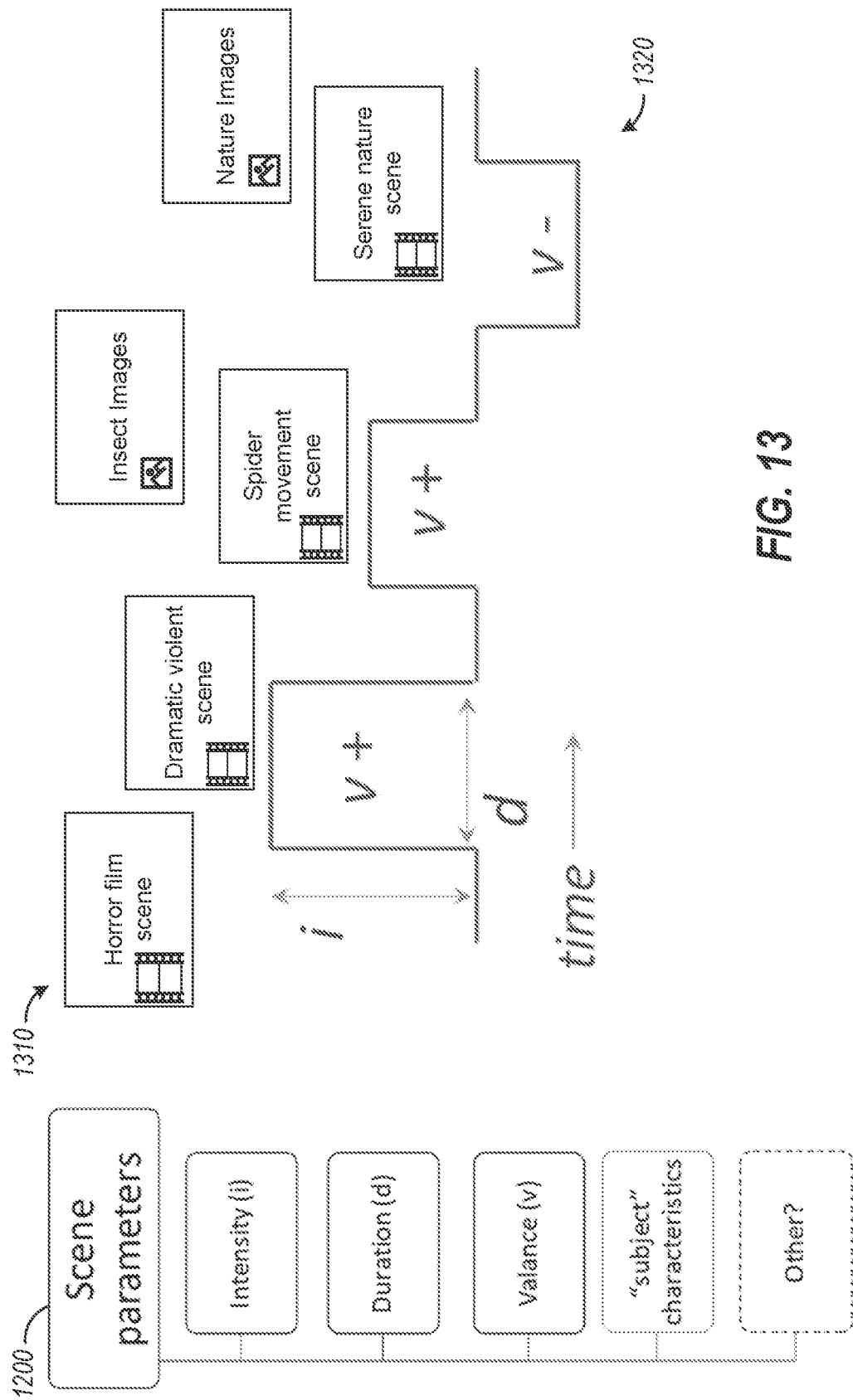
FIGS. 12 and 13 illustrate a data listing and charting of a scene response, respectively, according to an example.

FIGS. 12 and 13 respectively illustrate a data listing and respective charting of example scene emotional responses. The data listing in FIG. 12 shows how various scene parameters 1200, such as intensity, duration, valence, and subject characteristics, may be tracked for a particular scene. The charting of FIG. 13 depicts how a series of scenes 1310 with varying intensity (both positive intensity, and negative intensity) are handled over a period of time, with variations to these scene parameters. As a result, the various content (e.g., ghost, spider, serene lake) in the scenes can be defined by characteristics of the physiologic signals 1320 they induce.

FIGS. 14A to 14D illustrates a charting of example characteristics of physiological signals relative to scenes. With FIG. 14A, a comparison of scene-induced physiological signals, relative to multiple scenes with the same stimulation value, shows that cognitive state measurement will change with scene, time of exposure, and other factors in quantitative, predictable ways. With FIG. 14B, a comparison of scene-induced physiological signals, relative to multiple scenes with the different stimulation value, shows how the use of different stimulation values may correspond to different intensities or degrees of activation. With FIG. 14C, multiple scenes of stimulation with different valence or direction of activation (e.g., in excitatory or sedative directions), may be compared to different directions in a measured response. With FIG. 14D, multiple scenes of stimulation with different duration (e.g., longer or shorter clips of media content) may result in different types and gradients of physiological responses and overall responsiveness.

Figure 16:
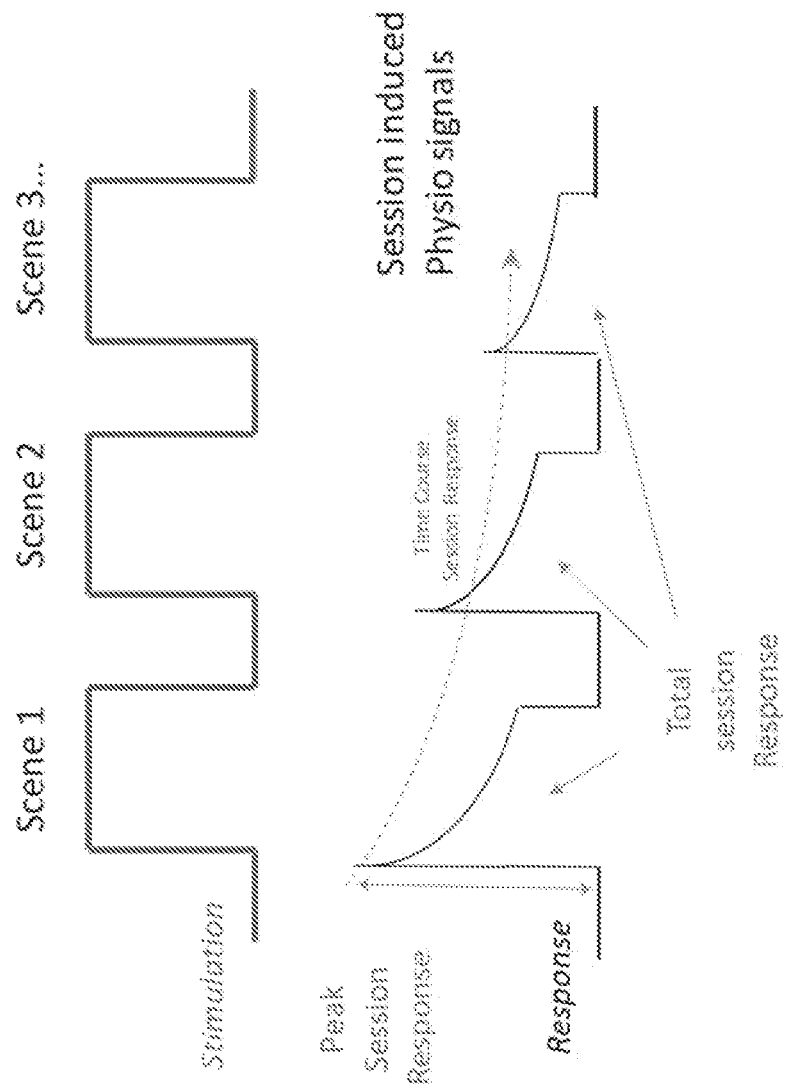
FIGS. 15 and 16 illustrate a data listing and charting of physiological signal characteristics, respectively, according to an example.
Figure 15:
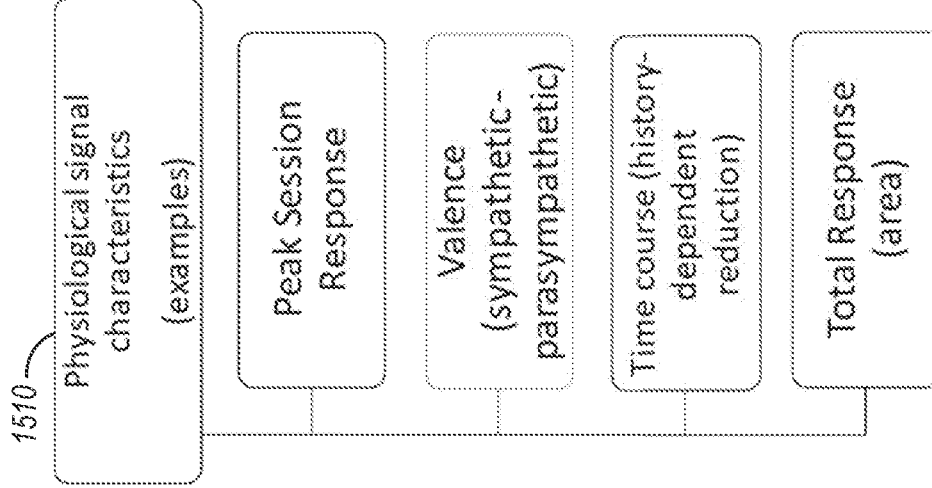

FIGS. 15 and 16 respectively illustrate an example data listing and charting of physiological signal characteristics. The data listing of FIG. 15 shows tracking of characteristics of physiological signals 1510 relating to peak session response, valence or emotional state such as anxiety vs relaxation or calmness or aversiveness vs attractiveness of a situation or (e.g., parasympathetic/sympathetic balance), time course (e.g., history-dependent reduction) and total response (e.g., measured over a response measurement area). The charting of responses occurring in FIG. 16, occurring with stimulation using successive scenes, depicts how a total session response will vary and change over time even with the similar valence or content stimulation. In particular, this demonstrates how stimulation repetition with repeated scenes or successive delivery of scenes containing similar content or valence levels and will impact responsiveness—generally decreasing responsiveness.

With a quantified control of content selection and output, clinicians can prescribe specific content, target responses, target response durations, levels, slope or ramping increase rate of change in responsiveness, pauses, repetitions, and other specific patterns of desired physiologic markers and changes. These specific goals can include time courses of seconds, minutes, or hours for intra-session markers. Specific goals can include time courses of days, weeks, or months for effects of overall therapy sessions or regimens. The algorithm will choose the specific scenes and the sequence of scenes that meet the clinician's prescribed stress patterns such as increasing stress over time, successive patterns of responses, specific classification or category of media content such as content depicting spiders, height or views from high angles, views of airplane interiors or scenes depicting airplane flights, closed or confined spaces or other specific situations that may be regarded as phobia related or specific anxiety inducing scenes or situations for an individual. Scenes and sequences may change in real time to titrate the sensory exposures to the target patterns. As a result, the therapy selection system will monitor responses and summarize responses for clinician review and annotation as needed. The therapy selection system may recommend to the clinician what sort of scenes and sequences to use next after reviewing the results of preceding treatment sessions.

Figure 17:
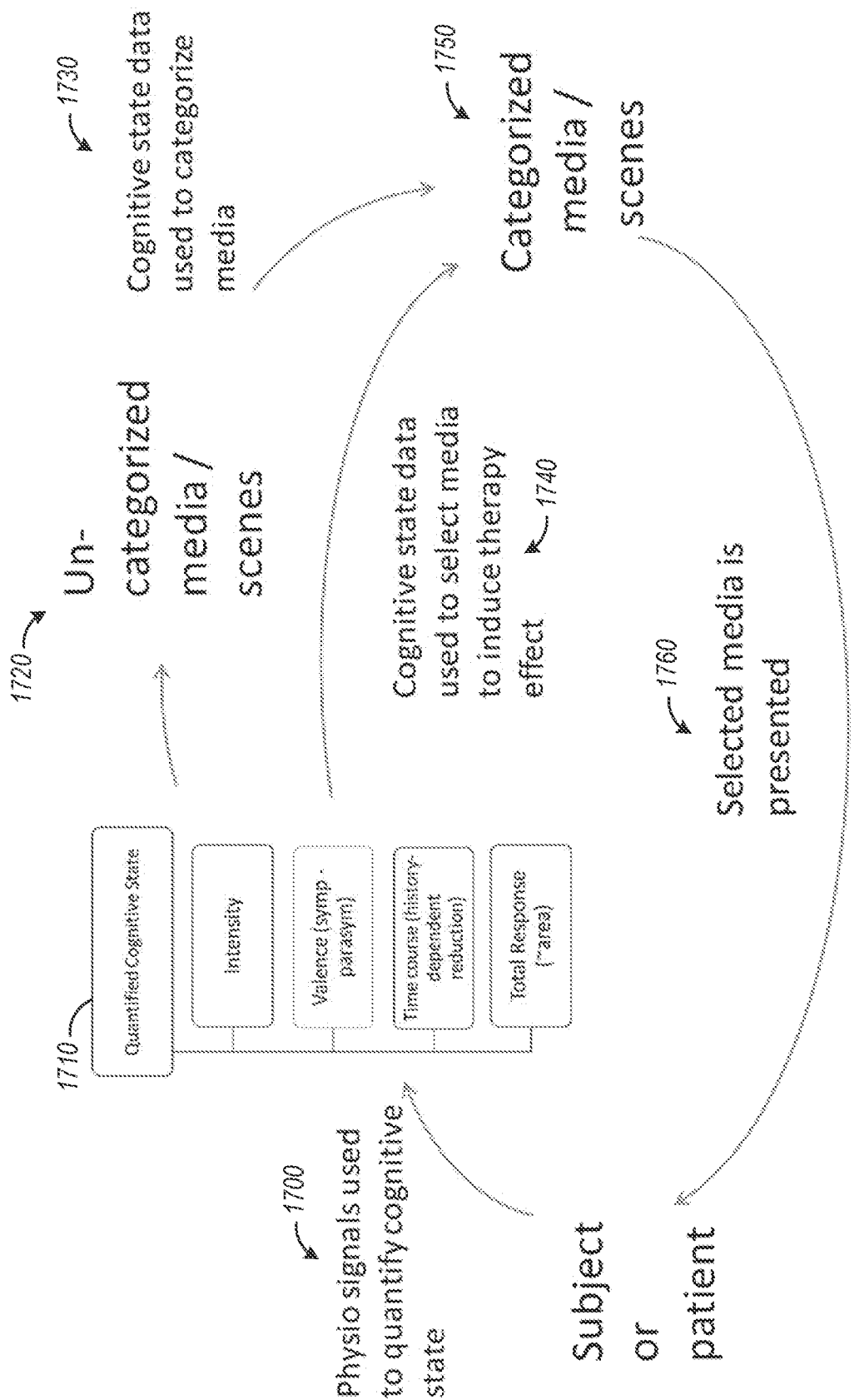
FIG. 17 illustrates an operational sequence between values of a cognitive state and operations performed as part of a therapy session, according to an example.

FIG. 17 illustrates an example operational sequence for content selection, based on values of a cognitive state and operations performed as part of a therapy session. As shown, the data values 1740 of the quantified cognitive state 1710, which are correlated to intensity, valence, time-course, and total response, are produced from a combination of physiological signals 1700. The cognitive state data values 1740 are used to select media that induces the therapy effect, using categorized media content and scenes 1750.

Notably, FIG. 17 also illustrates that uncategorized media content and scenes 1720 may be introduced and mapped to the cognitive state data attributes. Thus, when new content is identified for inclusion, the new content may be categorized with data values 1730 that identify intensity, valence, time course, and response data values, among others. (Such new content may be analyzed with a trained content analysis model, for example, to identify the cognitive state characteristics). The new media and scenes, once categorized, then may be selected for output 1760 to the human subject. This process allows the addition of content which the human subject has not seen, and has not become desensitized to.

The digital content or video library (e.g., a media library) will need to be quantified and cataloged in terms of potential cognitive responses to the content. In many prior approaches, digital content is cataloged by manual methods or oral or keyed input (language or symbol based) to characterize content. With the present therapy selection system, it is important that digital content can be characterized and catalogued (e.g., stored with reference to characteristics and potential uses) from automated characterizations based upon cognitive responses. The physiological responses captured will be stored and used for catalog reference in selection of future content.

Likewise, once expected cognitive outcomes for specific content segments are identified, artificial intelligence and image analyses methods may be used to automate potential methods for determining cognitive content in new digital material. For instance, the database can be used to model and test potential AI, machine learning, or other automated visual analysis approaches, as well the addition of new content. New forms and types of digital materials can also be screened and selected and presented to patients and subjects to measure responses and compare against predicted responses.

In some examples, the media content used for exposure therapy may be selected from existing video databases (e.g., video services of no cost to the public) such as YouTube (video commons), Google Video, Vimeo, Vidyard, Wisita, and the like. In other examples, proprietary or copyright-protected content can be viewed, as relevant selection data content (physiological data) is kept in a separate database or data service. In still other examples, patients could also access videos for exposure therapy and treatment purposes from subscription services, such as Amazon Video, Netflix, or Apple Video, as the therapy selection system augments the content with separate databases based upon cognitive physiological responses to the material. In another example, an internet bot, web crawler, crawler, spider or spiderbot could be used to systematically browse the world wide web for the purpose of web indexing or web spidering to update video content or index the content on a third party's site of web content, copy pages for processing by a search engine and apply indexes to the downloaded pages. Examples of web crawlers include the following: Googlebot, Microsoft BingBot, FAST Crawler, GM Crawl, PolyBot, RBSE, SortSite, Swiftbot, WebCrawler, WebFountain, Mercator, WebRACE, World Wide Web Worm, Xenon, and Yahoo! Slurp, Frontera, GNU Wget, GRUB, Heritix, ht://Dig, HTTrack, mnoGoSearch, Norconex HTTP Collector, Apache Nutch, Open Search Server, PHP-Crawler, Scrapy, Seeks, StormCrawler, tkWWW Robot, Venom, Xapian, YaCy, Octoparse, and Gnutella.

The usage and display of content with the therapy selection system may be supported by any number of fee models for therapy activities, including subscription or pay per use approaches. The therapy selection system may track exposures found by users via their own search (e.g., in a publicly available service), and enable the tagging of content so that other users of the therapy selection system may utilize the tagging information. Other data or functional aspects of the therapy selection system can also be shared with database or information system owners as a potential add-on capability, or need for use in therapies or other cognition-based uses.

As suggested by the examples provided above, therapy activities may occur as part of a clinician-prescribed therapy session, supervised assignments, homework assignments, on demand tasks, maintenance therapy (on-demand or assigned), or like variations. The therapy activities may be provided through a user interface on a mobile computing device (e.g., smartphone or tablet app), a website, an augmented or virtual reality device, a standalone or installed software application on a personal computer or smart device, or the like. A variety of interfaces may be developed to suit different types of devices and device capabilities for presenting content and measuring user responses.

Figure 18:
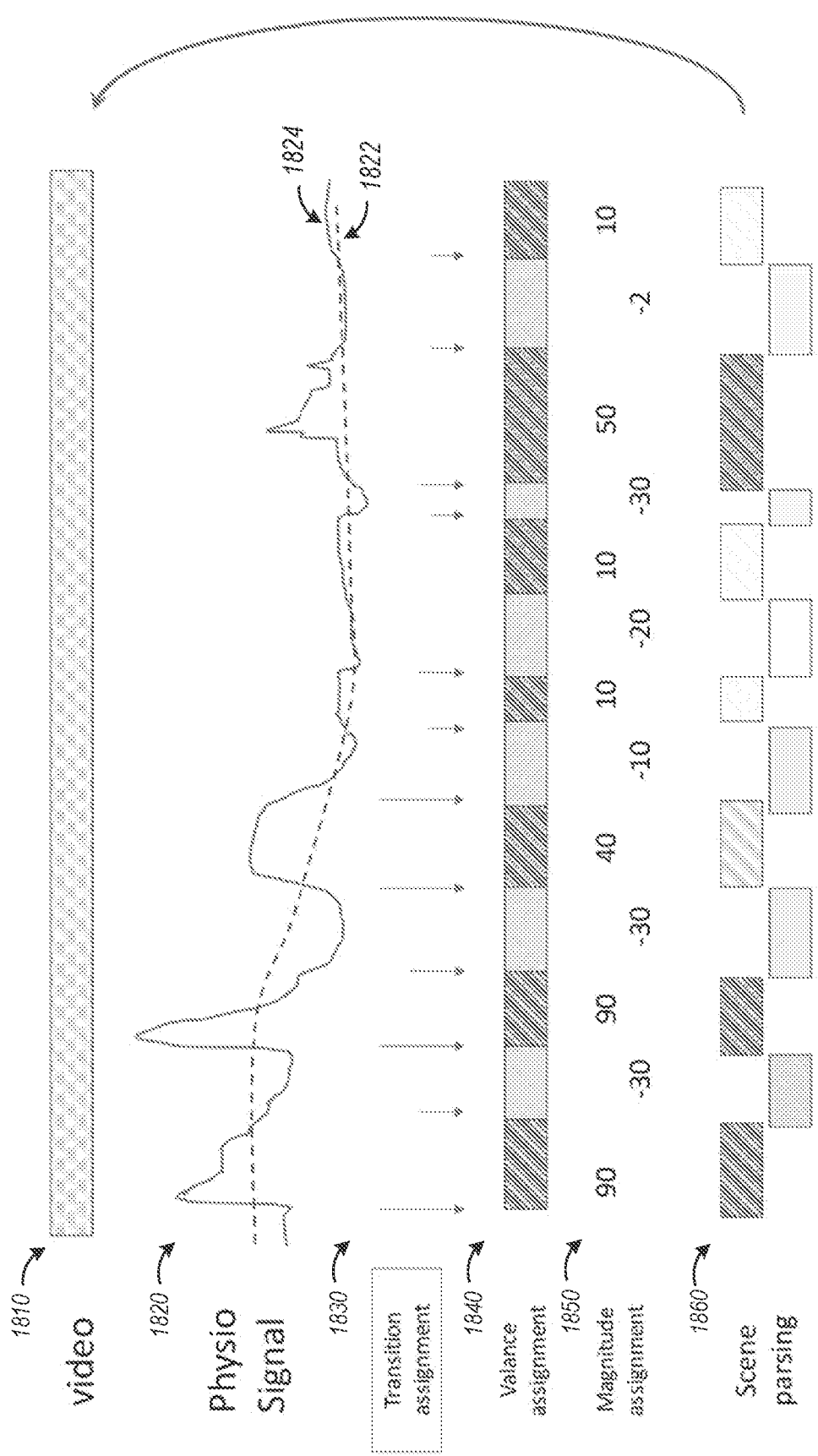
FIGS. 18 and 19 illustrate mappings between features of a video clip and associated physiological values, used as part of a therapy session, according to an example.
Figure 19:
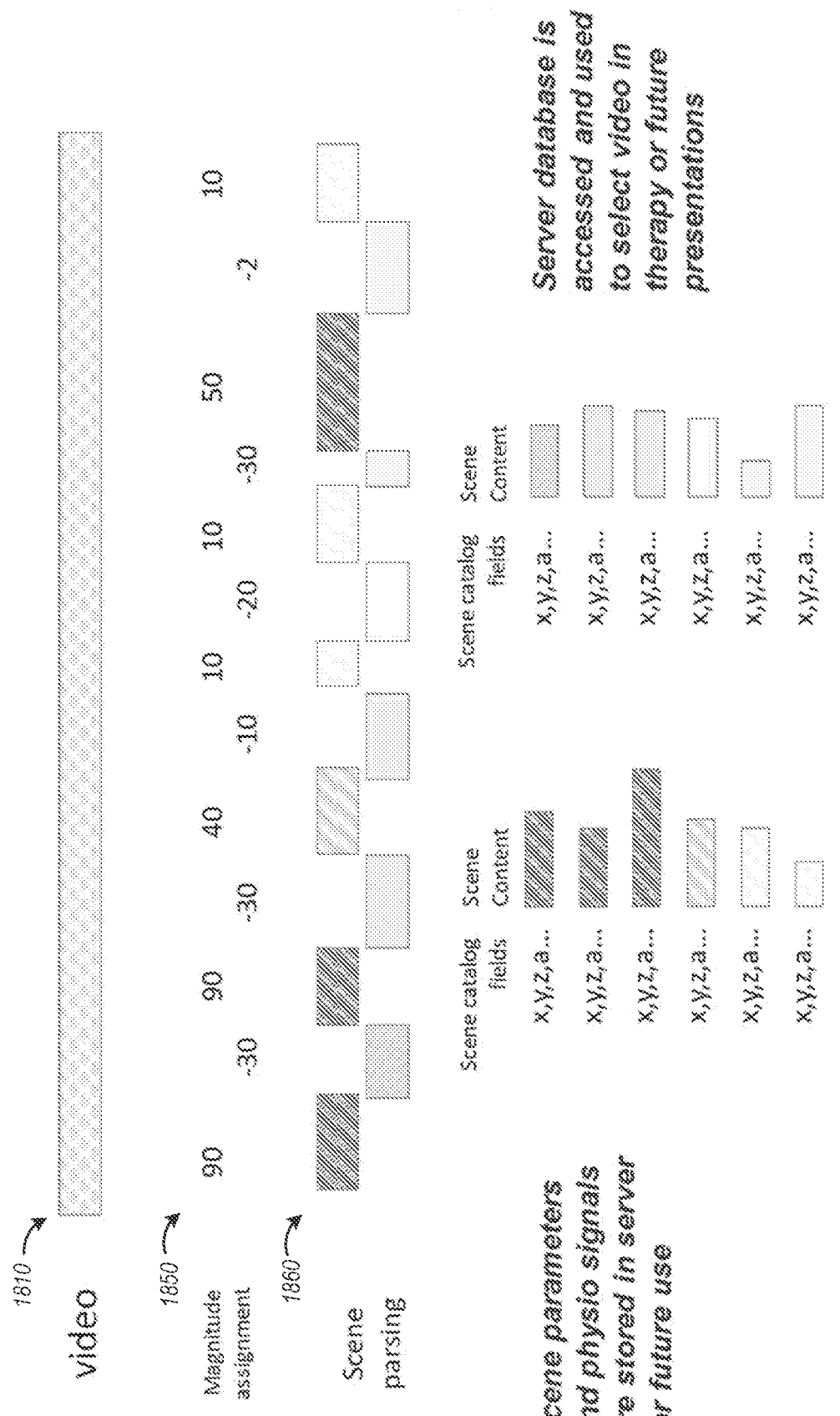

FIGS. 18 and 19 illustrate mappings between features of a video clip and associated physiological values, used as part of a therapy session. In the example of FIG. 18, various aspects of a video clip are segmented into different scenes, using scene parsing techniques. Each of these scenes is analyzed to provide a measurement of intensity (e.g., magnitude score) and direction (e.g., valence assignment). Thus, on a scene-by-scene basis, scenes with different scores may be evaluated and tracked. The video clip 1810 is shown with time as the x axis. Portions of the clip or other sensory stimulation series are associated with specific cognitive and emotional states in a subject that views the video. The Physio Signal 1820 is induced over time and captured using one or more physiological sensors or in combination with other sensors of attention or other aspects of the subject. The Physio Signal or signals will include short term or more rapidly changing components 1822 as well as overall average signals or other temporally slower components 1824. The Physio Signals and combinations of these signals can be used to define transitions 1830 between distinct portions of the video or sensory stimulation series that demarcate larger or smaller changes in cognitive, emotional or valence state based upon the magnitude or other measurement characteristics of the state transitions. These transitions can be associated with specific events or measurements within the video or sensory series to confirm temporal relationships or synchronization of the measurements to the presented series. A Valance Assignment 1840 or similar cognitive or emotional measurement can be assigned to each transition and the time period between each transition based upon similarities or differences between the measured state and Physio Signals and those measured in a population of normal subjects or subjects with specific conditions. The Magnitude Assignment 1850 can be made for each period or portion of a period between each transition assignment to quantify the level or degree of cognitive, emotional or valance state during the measurement time. The Magnitude Assignment 1850 and specific measurements can then be used to assign expected human or subject responses or states and degrees of states to the video clip or sensory stimulation series as scene parsing 1860. The parsing or designation of a scene, clip or quality thereof can be on the basis of expected responses induced from normal humans, or according to subtype or condition of humans, humans with specific conditions or prior experiences or treatments, or with specific vocations or avocations, medical or psychological conditions or injuries. These assignments can be then be used to establish a catalog 1910 and the assignments can be subsequently used in a selection process or algorithm to identify and select specific videos, segments of videos, clips or other sensory stimulation series or qualities for presentation to subjects for future uses and needs.

A video or other digital media may be presented to a subject either as a complete work or in scenes or selections. As the media is presented physiological monitoring will be used to identify transitions of psychological state or autonomic state associated with the digital media. Magnitudes of valence or emotional state or anxious or aversiveness vs calmness, relaxation or attractiveness induced by successive scenes will be captured. The psychological states or autonomic states induced will serve as a score that will be cataloged or assigned to specific content, scenes and works. Future use of the media and scores in exposure therapy or other commercial uses can be facilitated by the scores.

The analysis of individual scenes and scores may enable use and analysis of observed physiological results in a variety of therapies. For instance, such uses may include: a use of system in open loop applications for therapy, including use with or by a clinician during a therapy session; use of system by a patient to guide homework sessions using digital media; use of system by patient during in vivo sessions in real world settings such as during field trips designed to provide exposures, or during a patient's routine or planned individual use in daily activities and experiences; use by patient or patient's clinician or patient's family member or patient's employer or school or health care organization or health insurance company as an early warning system—to alert them of developing anxiety state; use of the system by a patient with behavioral or other psychological therapies to treat developing and actual states; use of the system with interoceptive exposure therapy; use in dosing or titrating other therapies, including in combination with other forms of therapeutic, behavioral, neurostimulation, ablation, medication, and other methods for treating conditions.

In the example of FIG. 19, a further breakout of scene content in a catalog 1910 is presented for respective scenes, and is correlated to physiological signals. In an example, various patient responses are used to mark and categorize the scenes, and establish, improve and create a usable database of scenes or scene types. Each scene or clip or portion of the clip or scene will induce a response that can be quantified using a tracked score such as a physiological anxiety state (PAS). The timing and series of responses to the clip or scene can be related to the presentation timing to synchronize or ensure synchronization of the multiple data streams. Specific measurements of the video or sensory series or the time stamp of the video or sensory series can be used. Additionally, measurements of the physical characteristics of the video or sensory series can be captured during the presentation and used to create and confirm proper synchronization of the signals for valid assignment of measured responses to the content.

First, scene-specific scores are created for scenes based upon effectiveness at inducing responses in all patients and in specific subtypes of patients defined by patient specific signature classification.

Second, relative differences between or changes in responses are used. Patient responses to scenes are captured. Classes of scenes are differentiated based upon general and specific responses. Specific clips within scenes can be noted and differentiated. Each temporal segment of a scene of as brief as 1 second or as long as 30-60 seconds may have specific coding for general and patient-type response.

Differences are maximized between scenes. The system can present successive scenes to patients based upon quantifying outcomes and determining a scene repertoire that covers a spectrum or spread of patient responses. Randomly selected new scenes can be used to quantify responses magnitude and type for new database development. Quantitative expected response characteristics can be created and used in future tests of scenes and patients.

A scoring system can be developed to quantify the balance of sympathetic and parasympathetic activity for any point in time. The scoring system may be absolute, or calibrated to a patient's baseline prior to initiating therapy. The scoring system can be applied to track patient response relative to other patients viewing the same scene. The scoring system may also be used to label scenes on a second by second basis as the same scenes viewed by others from normal patients to patients with varying severities of anxiety. As more and more individuals view the same scene, the quality and variance of the data will improve.

A history dependent score, based on occurrences within session history and between session histories, may also be utilized within the scoring system. Time course of response and responsiveness to anxiety stimulation within a session can be tracked and used to track progress within the session on time orders of seconds to minutes to hours. In general, subsequent stimulation of an anxiety inducing scene or clip will induce a reduced anxiety signal. The time course for reduction can be rapid or slow and may be correlated with the severity of the patient anxiety diagnosis or quality of anxiety. Within a duration of exposure, a patient may show a decrease in stress response. Presentation of a stress agent may be useful to reinitiate a response, but a subsequent response may be reduced due to desensitization or therapy benefit. Time course of response and responsiveness between sessions can be tracked and used to compare progress over durations of time of days, weeks, months or years.

In addition or in substitute to the presentation of video content, relevant sensory stimulation delivered to the patient from the therapy selection system could include many forms of a sensory stimulus or stimuli (including those previously discussed), such as auditory, visual, audio-visual, light patterns, virtual reality, augmented reality, tactile or mechanosensory including both external or internal (interoceptive), vestibular, thermal or temperature changes or levels, olfactory or scent, gustatory or taste-based exposures, electrical, magnetic, electromagnetic, or combinations of any of the above. Stimulation with chemicals, mechanical stimulation, thermal stimulation or other stimulation (internal physiology focuses) or stimulation through sensory receptors are also possible. The stimulation may be varied in the form of a sequence of tones, music, volume, photos, images, videos, movies, tactile inputs, vibrations, rhythmic stimulation, written material, internet content, scents or olfactory, gustatory stimulations, or a combination of these inputs. Stimulation may be delivered via computer, laptop, tablet, mobile phone or other external device, speaker, smart speaker, monitor, screen, glasses, goggles, headphones, active garments, wearable devices, furniture, electronic/digital generators, or guided meditation or visualization.

Components of the sensing and control system can also be used to monitor human responses to real world experiences, specific experiences encountered in vocations or in certain professions, conversations, therapy sessions, or to imagined or introspective experiences generated within or experienced by a subject including meditation, guided visualization, or inner visualization. In these cases, the monitoring and measurement recordings would direct feedback recommendations provided to the subject or to a caregiver or medical provider that would then relay or act on the feedback to alter or change the introspective or real world experience for the subject to induce a new state or change in state of the individual for therapy or other application.

Although many of the previous examples refer to exposure therapy as a mechanism for treating phobias or other psychological conditions, it will be understood that other forms of treatment and therapeutic applications are possible. Moreover, the described framework for therapy selection and delivery may also have applicability to nontherapeutic applications such as education, training, entertainment, or advertising, among other fields of use.

Simulation Training. In further examples, the present systems and devices could be used for simulation training of personnel to perform in a high stress occupation such as a performer, actor, musician, comedian, athlete, commercial pilot, emergency medical technician, soldier, medic, paramedic, ambulance dispatcher, emergency physician, critical care physician, surgeon, obstetrician, doula, firefighter, police officer, or air traffic controller. The present systems and devices could be used for simulation training of personnel who trade items in the capital markets, including stocks, options, securities, bonds, debt, or commodities including metal, energy, agriculture, meat, or consumer goods. The professional would be exposed to a certain scenario by an interactive or passive audiovisual display. The professional would then be asked to manage the scenario by viewing visual content or interacting with a simulator. Scenario content or series of sensory stimulations or videos would be chosen and then adjusted in real time by a decision algorithm in response to the professional's pattern of sympathetic, parasympathetic or net sympathetic-parasympathetic response to reach a target pattern of autonomic activity. The scenario content would vary over time, perhaps changing on a second-to-second or minute-to-minute basis so that the physiologic response induced by the scenario content would track a desired target pattern of autonomic activity.

For example, if an objective is to provide a medical trainee with practice dealing with an unexpected medical decompensation of a patient, the video scenario of a simple cough could progress to chest pain, difficulty breathing, and then cardiac arrest depending on the trainee's physiologic response to each change in the scenario content. The objective of training is to provide the professional with experience of perceiving and making decisions while experiencing the stress of a difficult situation. Overwhelming the professional with stress early in the scenario would not be productive. Instead, the scenario would evolve as the professional tackles increasingly stressful situations. Ultimately, the professional would not become stressed when exposed to these scenarios. Another example is training of police officers by titrating visual content using physiologic signals so that police officers remain calm during stressful situations. Such training would reduce the likelihood that a police officer would escalate a stressful situation by threatening, yelling, physically confronting, tackling, choking, or shooting an individual when such action is not warranted. In some circumstances over-reaction to stressful situations can be sensed so that additional training or screening methods can be employed to avoid future unwanted situations.

Video Games. In further examples, the present systems and devices could be incorporated into video game environments. The gamer would be exposed to a certain scenario by an audiovisual display such as a video screen or virtual reality system. The game would unfold to become more or less difficult, more or less scary, or more or less engaging to reach a target pattern of autonomic activity. The target pattern of autonomic activity would vary over time, perhaps changing on a second-to-second or minute-to-minute basis. If an initial level of gaming difficulty is "easy" for the gamer, his physiologic response would reveal relatively low levels of sympathetic activity. The degree of difficulty or type or content of the game would be adjusted to achieve a desired pattern of autonomic activity representing a target state of excitement or cognitive engagement. Should the gamer's stress level subside at one degree of difficulty, the decision algorithm would progress to a more challenging degree of difficulty or altered presentation method, titrated to achieve and maintain a target pattern or level of autonomic activity. The specific characteristics useful to engage and maintain cognitive engagement of a specific individual can be stored and referenced and used to facilitate future exposure experiences.

Gambling. In further examples, the present systems and devices could be games or an online casino while gamblers play video betting games such as slots, roulette, blackjack, craps, or poker. A target pattern of autonomic activity could be established for a specific gambler to maintain the gambler's interest so that he continues to gamble. The game would result in a pattern of wins and losses, including varying sequences and financial levels of wins and losses, to achieve a target level of autonomic activity known to maintain a gambler's interest and maximize long term profits for the casino. The target level autonomic activity could be developed from populations of gamblers sharing similar levels of physiologic sensitivities, or could be individualized to one specific gambler based on his pattern of physiologic response noted through previous gambling sessions. If the physiologic response of the gambler suggests he is growing bored of a particular game, the game could automatically switch to another game, or a series of games, or the delivery method or type of game can be altered until the gambler's physiologic response suggests his interest and attentiveness has been restored. If the physiologic response of the gambler suggests he is becoming demoralized or stressed from excessive or too many losses, the decision algorithm would cause the device to deliver a financial win. The specific characteristics useful to engage and maintain cognitive engagement of an individual can be stored and referenced and used to facilitate future gaming experiences.

Predictive Interactions. In another example the system or sensing stressful or cognitive state from physiological signals can be used in human-machine interactions to allow technologies to predict and define situations and responses to situations before they occur or more rapidly after they occur. As technologies become available to utilize technological sensors independent of humans, such as driverless cars and autonomous vehicles, sensing of stressful or cognitive state in humans within or near to these vehicles can allow these autonomous systems to include human reactions and responses over time. For example, humans riding in a driverless car or public transportation can be monitored. The human reactions to the situations or experiences in the vehicle can be used to alter the responses of the vehicle or vehicle monitoring system to reduce stress or alter the human experience as desired. The specific characteristics useful to alter the experience or cognitive engagement of an individual can be stored and referenced and used to facilitate future vehicle experiences or to enhance the safety responses of the vehicle.

Video. In further examples, the present systems and devices could be incorporated into a video streaming service to maintain a viewer's interest or induce a target pattern of autonomic activity while watching a series of video clips, television shows, commercials, or on-line video content offered by cable or streaming or video-on-demand video content. The genres of video content could include educational video, documentaries, pornography, or entertainment such as comedy, crime, drama, fantasy, horror, or science fiction. A target pattern of autonomic activity could be selected by the viewer, broadcaster, or video content site. Video content would be streamed to induce this target pattern of autonomic activity. The content could be changed in real time to reach the target pattern of autonomic activity. Videos could be made for this purpose with branching parallel sequences, so that the story could flow to one branch or another based on the viewer's pattern of autonomic activity. The specific characteristics useful to engage and maintain cognitive engagement of an individual can be stored and referenced and used to facilitate future video presentation experiences.

Shopping. In further examples, the present systems and devices could be incorporated into an e-commerce or online shopping service when viewing images. One such application is with on-line retail such as Amazon, Alibaba, Walmart, eBay, Otto, Jingdon/JD.com, Priceline, Flipkart, or Costco to maintain a shopper's interest while browsing or searching an on-line "store". For example, the site could target a pattern of autonomic activity that correlates with interest level. As a shopper browses a computer or mobile device, if the target pattern of autonomic activity or cognitive state is reached the site would continue to stream similar objects for the shopper to consider purchasing. These physiological response data may also be compiled and used in conjunction with other shopper data such as interactions with other shoppers or family or similar methods to better understand the shopper and their situation. If the target pattern of autonomic activity in a shopper is not being achieved, the site would display other items or methods of presentation or types of products for the shopper to consider based on the predicted physiologic response for that shopper to the items. The specific characteristics useful to engage and maintain cognitive engagement of a specific shopper or type of individual or their shopping situation can be stored and referenced and used to facilitate future shopping experiences.

Dating Services. In further examples, the present systems and devices could be used with an algorithm to select video images within dating sites. Smart streaming of images such as a head shot based or video clip based on a viewer's physiologic response could be used by dating websites such as Match.com, Eharmony, OkCupid, JDate, Badoo, Chemistry, or Tinder when presenting potential partners. A decision algorithm could learn what sort of features from a photo, video clip, voice recording, or write up induces a target physiologic response or target cognitive state for an individual viewer, and select candidate partners with those features. The specific characteristics useful to engage and maintain cognitive engagement or choice of the customer of a specific individual or type of individual or their dating situation can be stored and referenced and used to facilitate future dating or choices of potential date or experiences.

Search. Algorithm could be used with internet search engines such as Google, Google Chrome, Explorer, Firefox, Safari, Yahoo, Bing, AOL, Facebook, YouTube, Wow, WebCrawler, MyWebSearch, Infospace, Excite, Quant, Wikipedia, Blekko, Crunchbase, CC Search, DuckDuck Go, Technorati, Ask.com, Baidu, Yandex or other search engines. As a subject reads or views or listens to content, the subject's physiologic response signals would be measured in real time or within a delay of milliseconds, seconds, or minutes and associated with the content that is being read or viewed or listened to. A decision algorithm could learn what sorts of features from the content induces a target physiologic or cognitive response for an individual viewer, and select additional content for the subject to read, view, or listen to.

Boost efficacy of other therapies. In further examples, the present systems and devices could be incorporated into a therapy delivery system or used in conjunction with another therapy or therapies such as rehabilitation, physical and occupational therapy, drugs, medication, psychotherapy, or brain stimulation. Brain stimulation methods include transcranial magnetic stimulation (TMS), deep TMS, transcranial direct stimulation, transcranial ultrasound, deep brain stimulation, cranial electrotherapy stimulation, electroconvulsive therapy, magnetic seizure therapy, and vagus nerve stimulation. In these examples it is important for the cognitive state of an individual to be monitored and controlled to specific states to optimize the therapeutic impact of the therapy and parameters of therapies. In this setting a desired cognitive state is induced and maintained by a sensory delivery system and then therapeutic interventions can be effectively delivered for maximum impact on the desired disorder. For example, the sensory therapy delivery system could target a pattern of autonomic activity that correlates with optimal cognitive state or level of autonomic activation required for maximal therapy efficacy. As a patient's autonomic activity is monitored the sensory stimulation can be delivered to achieve specific targets or types of activities that are most conducive to effective therapy or specific types of therapy. Sensory stimulation can be modulated to test effectiveness of the therapy as well as cognitive state and autonomic state. These physiological response data may also be compiled and used in conjunction with other patient data or similar methods to better understand the patient and their needs for therapy. The specific characteristics useful to engage and maintain cognitive state of a specific patient or type of patient with a specific disorder or their therapy delivery situation can be stored and referenced and used to facilitate future therapy.

Auditory Therapeutic. In further examples, the present systems and devices could be used to automatically select or modify an auditory stimulus to modulate the physiological activity or cognitive state of a human subject to a desired physiological activity or cognitive state based on the physiologic response signals of the human subject while exposed to the audible stimulus. For example, music or spoken word or audible book readings or meditations or mindfulness narratives or poetry readings could be streamed through a speaker such as Amazon Alexa, Google Home, Sonos, or Apple HomePod, through headphones, ear buds, personal speakers, car speakers, mobile devices such as a tablet or mobile phone, or through neural stimulation inputs including direct cochlear nerve stimulation. Similarly, soothing sounds such as white noise, pink noise, rain drops, pouring rain, distant thunder, thunderstorm, wind, trickling water, ocean waves, waterfall, stream, brook, creek, stream, crickets, insects, frogs, chirping birds, wind chimes, fire, dolphins, whales, womb sounds, or voices could be streamed through the devices listed in the previous sentence.

The audible stimulus could be selected, changed, altered, or stopped based on the physiologic response signals after the auditory content has started to play. In the case of music, the physiologic response signal to one song could be used to select a subsequent song and determine appropriate time for ending the music. Elements of the musical stimulus could be altered in real time while a song is playing based on the physiologic response to elements of the music stimulation.

Elements of the music stimulus that could be selected or altered include qualities of one or more of the following: song, song arrangement, song list, song order, genre, artist, singer's vocal range or vocal type or accent, composer, title, lyrics, melody, harmony, rhythm, form, composition, chorus, length, consonance, timbre, tempo, orchestration, instrument or instruments, prominence of specific instruments or voices, volume, dynamics, instrumentation, tone, tonality including major or minor or atonal, harmony, rhythm, syncopation, time signature, phrase length or shape (e.g. arch, spiky) or structure, Form (e.g. binary, ternary), ritornello, repeated baseline, equalization, frequency content of an audio signal, specific frequency bands or ranges, frequency response, amplitude of audio signals at specific frequencies, attenuation or emphasis of certain frequencies, acoustics, or a subject's prior indication of liking or disliking a song, or ratings of a song by other subjects with similarities in profile such as age, demographics, physical condition, or medical history).

A musical stimulus could be drawn from a digitally stored music collection of a subject or subject's family, school, club, housing facility, employer, clinician, clinic, hospital, nursing home, or healthcare provider. Music may also be accessed through one or more streaming databases such as Sirius, Sirius XM, Pandora, Spotify, Apple Music, Amazon Prime Music, Amazon Music Unlimited, Google Play Music, Slacker Radio, Tidal, YouTube Music, Sound Cloud, iHeart Radio, TuneIn radio, Deezer, Rhapsody, 8tracks, AccuRadio, Anghami, Bandcamp, Earbits, hoopla, Jango, Joox, Line Music, Music Choice, NetEase, Roxi, or Stingray Music.

Through a method of presenting music, testing and development of a classification of music and elements of music, the present techniques may support the development of a database to store and catalog music based upon its predicted usefulness in inducing the desired autonomic responses. Thus, various techniques may involve presenting and learning how the crowd (a population of individuals) including segments or subsets of the crowd are predicted to respond to the music based upon prior testing or based upon predictive algorithms developed through the present techniques, or based upon how an individual reacts physiologically to elements of the music stimulus. Algorithms may catalogue how a particular subject for any given physiologic or cognitive state has previously responded to particular elements of a music stimulus, and refer to this catalogue of past responses to help determine whether certain a certain music stimulus is likely to induce a desired physiologic response or cognitive state in that subject, or in other subjects.

AI, neural networks and other forms of machine learning can be used to assign a score to musical tracks to build the databases needed to predict what will induce a net parasympathetic nervous system activity in typical humans, or subsets of humans (e.g. age, peer group, demographic, musical taste, location, experience, weight, BMI, medical history, current illness, medication drug or cigarette or alcohol or marijuana use, education, previous exposure). Ongoing presentations and sensing will be used to update the database over time to allow for changes in musical tastes or parasympathetic response characteristics over time in a population.

Level of sympathetic-parasympathetic activity or physiologic response signals or cognitive state detected in real time by sensors will guide the selection of elements of the musical stimulus. In addition the music can be automatically screened by artificial intelligence models, neural networks or similar machine learning methods to allow the system to automatically select potentially useful music from a database. Subsequent inclusion of this music in testing can confirm or disaffirm the utility of selected elements of the musical stimulus in modulating the autonomic nervous system, physiologic state, or cognitive state. Additionally elements of the music stimulus can be included in testing to explore which elements can be quantified and selected for utility in the selection method as well as for future use as presented music to control autonomic functions.

A spoken word stimulus could be drawn from a digitally stored collection of verbally recorded books, readings, speeches, poems, podcasts, articles, stories, mediations, and the like. Such material may be accessed from Audible.com, a podcast host such as RadioPublic, PodBean, Blubrry, Sound Cloud, Podomatic, Spreaker, ZenCast, Simple Cast, Audioboom, Spotify, Apple, iTunes, or recorded talks on TED.com YouTube, Netflix or Amazon Prime Video. Spoken word stimulus could also consist of recorded meditations that could be streamed from a mindfulness application such as HeadSpace, Calm, MindBody, Buddhify. Smiling Mind, Yogaglo, or Ensō.

In the case of a meditation, the physiologic response signal to one meditation could be used to select a subsequent meditation, or to alter in real time elements of the meditation. Elements of the meditation stimulus could include elements of a musical stimulus, as well as subject matter, length of recording, the narrator, background music, subject's past experience listening to the narrator, narrator speech characteristics such as style, speed, volume, dynamics, accent, sex, and pitch, and the sequence or order of multiple spoken word materials, physiologic responses of others with similar mental state to that meditation, and an individual's AI predicted response to that meditation.

Through a method of presenting spoken word stimuli, testing and development of a classification of the spoken word content and segments of the spoken word content, the present techniques may support the development of a database to store and catalog spoken word content based upon its predicted usefulness in inducing the desired autonomic responses. Further techniques may include presenting and learning how the crowd (a population of individuals) including segments or subsets of the crowd are predicted to respond to the spoken word content based upon prior testing or based upon predictive algorithms developed through the present techniques, or based upon how an individual reacts physiologically to elements of the spoken word, including subject matter, length of recording, the narrator, background music, subject's past experience listening to the narrator, narrator speech characteristics such as style, speed, volume, dynamics, accent, sex, and pitch, and the sequence or order of multiple spoken word materials.

AI, neural networks and other forms of machine learning can be used to assign scores to written word material to build the databases needed to predict what will induce a net parasympathetic nervous system activity in typical humans, or in subsets of humans (e.g. age, peer group, musical taste, location, experience, weight, BMI, medical history, current illness, drug or cigarette or alcohol or marijuana use, education, previous exposure). Ongoing presentations and sensing will be used to update the database over time to allow for changes in written word taste or parasympathetic response characteristics over time in a population.

Level of sympathetic-parasympathetic activity detected in real time by sensors will guide the selection of written word content, narrator, title, length of piece, and related characteristics of specific written word content. In addition the written word material can be automatically screened by artificial intelligence models, neural networks or similar machine learning methods to allow the system to automatically select potentially useful written word content from a database. Subsequent inclusion of this written word content in testing can confirm or disaffirm the utility of the selected written word content in modulating the autonomic nervous system, physiologic state, or cognitive state. Additionally components of the written word content such as tempo, volume, dynamics, instrumentation, voice type, pitch, syncopation, or type of musical accompaniment, can also be included in testing to explore which elements can be quantified and selected for utility in the selection method as well as for future use as presented written word content to control autonomic functions.

As will be understood, many people suffer diseases related to imbalance of the autonomic or sympathetic or parasympathetic nervous systems, including chronic over-activity of the sympathetic nervous system, chronic under-activity of the parasympathetic nervous system, a relative imbalance of sympathetic activity versus parasympathetic activity, or inappropriate reaction or sensitivity of the autonomic nervous system to stressful conditions. The resulting chronic over-activity of the sympathetic nervous system is believed to exacerbate disorders across a variety of physiologic systems including the cardiac, vascular, renal, metabolic, immunologic, endocrine, respiratory, neurologic, and gastrointestinal systems. Clinical disorders exacerbated by relative sympathetic over-activity include hypertension (high blood pressure), heart failure, systolic heart failure, diastolic heart failure, heart failure with preserved ejection fraction, peripheral vascular disease, vascular aneurysm, angina, epilepsy, asthma, pain, rheumatoid arthritis, metabolic syndrome, Type 2 Diabetes, obesity, sleep disorders, irritable bowel syndrome, multiple sclerosis, immunological disorders and allergies, as well as certain psychiatric conditions such as anxiety and panic disorders. For example, individual with chronic pain may benefit from this therapy, including individuals suffering from musculoskeletal pain, neuralgia, arthritis, fibromyalgia, rheumatoid arthritis, inflammatory pain, non-inflammatory pain, nociceptive pain, or neuropathic pain, inflammatory bowel disease, cancer pain, bone pain, migraines, burns, shingles, multiple sclerosis, muscle spasm, etc. The inventors believe that automated, personalized selection or modulation of an auditory stimulus such as music or spoken word or audible book readings or meditations or mindfulness narratives or poetry readings or soothing sounds in real-time based on an individual's physiologic response to the auditory stimulus, may improve these and other chronic conditions.

Figure 20:
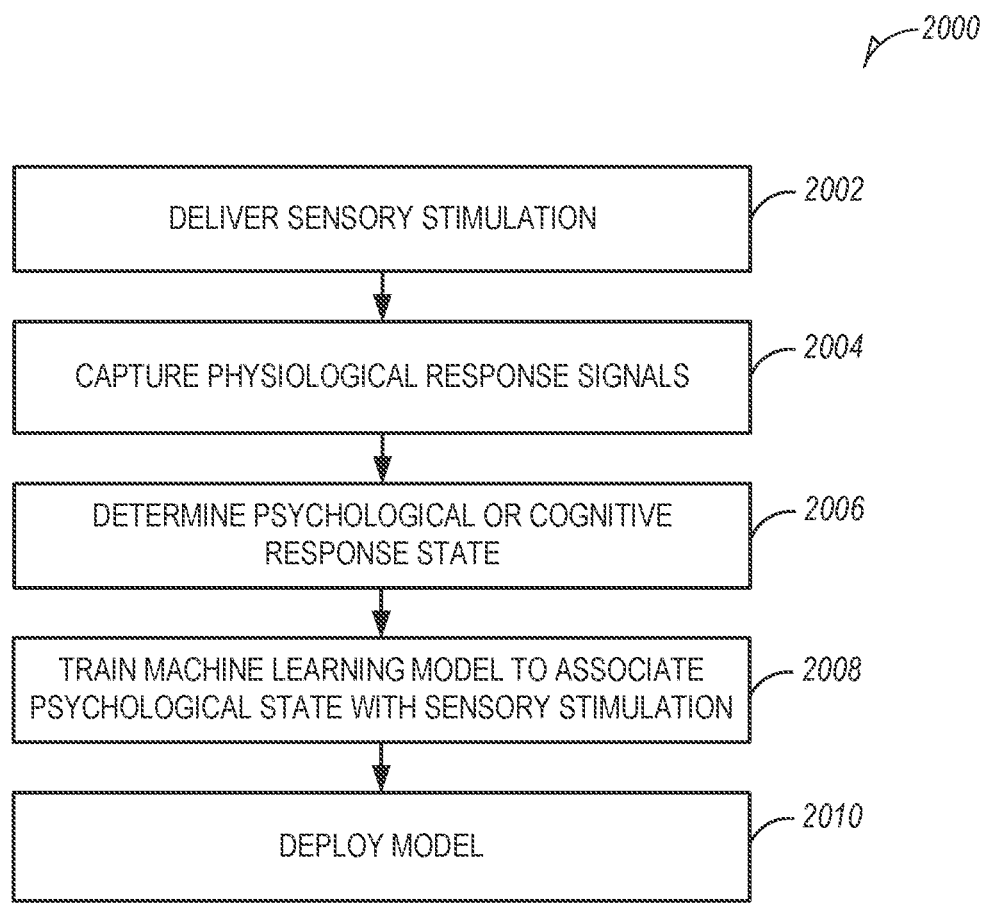
FIG. 20 is a flowchart of an example method for training a media content model for analyzing cognitive response of a human subject, according to an example.
Figure 21:
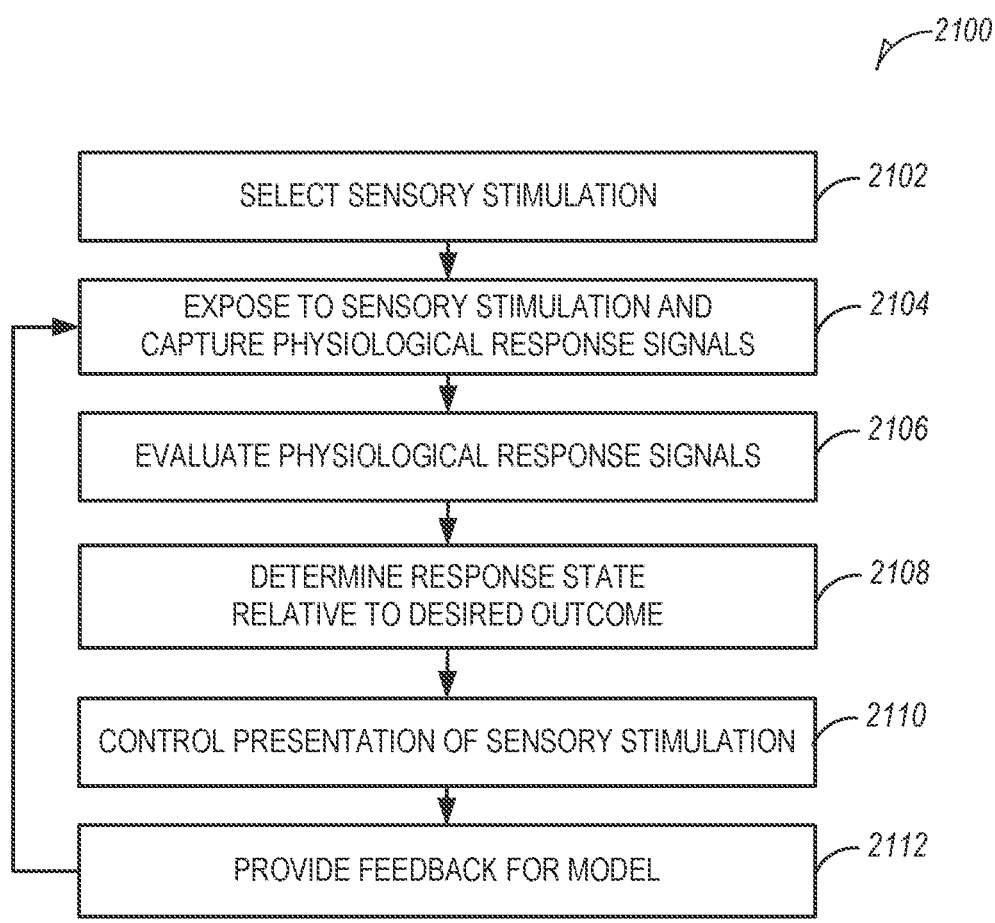
FIG. 21 is a flowchart of an example method for controlling therapy treatment of a human patient using presented media content, according to an example.

FIG. 20 is a flowchart (2000) of an example method for training a media content model for analyzing cognitive response of a human subject, such as in connection with the machine learning model discussed in the previous examples. The operational sequence of the flowchart is depicted as including:

1) Presenting sensory stimulation (2002) (e.g., a scene of media content) to the human subject.
2) Capturing physiological response signals (2004) from a human subject (e.g., during the presentation of the scene of media content).
3) Determining the psychological or cognitive response state (2006) of the human subject (e.g., from the physiological response signals).
4) Training the model (2008) (e.g., the machine learning model) to associate the response state with the stimulus (e.g., particular media content), and in some examples, a type of treatment.
5) Deploying the model (2010) (such as discussed with the use flowchart of FIG. 21).

FIG. 21 is a flowchart (2100) of an example method for modulating the physiological activity of a human subject, according to an example. For instance, such modulating may be employed as part of controlling an exposure therapy treatment for the human subject, using presented media content. Other types and kinds of therapy may also be utilized, as discussed herein. The operational sequence of the flowchart is depicted as including:

1) Select sensory stimulation (2102) (e.g., a scene of media content from a media library, or from a source of media content that is new to the system, which has not been analyzed before), such as with use of a decision algorithm (e.g., implemented in a trained classification model to predict an expected physiological response to a stimulus in the scene of media content).
2) Expose the subject to the selected sensory stimulation and obtain physiological response signals (2104) (e.g., during a presentation of a scene of media content).
3) Evaluate physiological response signals (2106) (e.g., obtained in response to the presentation of the scene of media content).
4) Determine the response state relative to a desired state or outcome (2108) (e.g., a desired psychological response, cognitive state, physiologic response, or symptomatic response).
5) Control the presentation of sensory stimulation (2110) (e.g., the scene of media content) based on the evaluated physiological response signals relative to the expected response state.
6) Provide feedback for the model (2112), as applicable.
7) Repeat operations (2104-2112), as part of a therapy or scenario (e.g., to observe a desired autonomic response to the stimulus).

In further examples, the presentation of the particular sensory stimulation (e.g., the scene of media content) may be used as part of a therapy where an objective is defined to first reach a desired outcome (e.g., a particular cognitive state) so that another therapy (e.g., that works best for patients in a particular cognitive state) can be administered.

Figure 22:
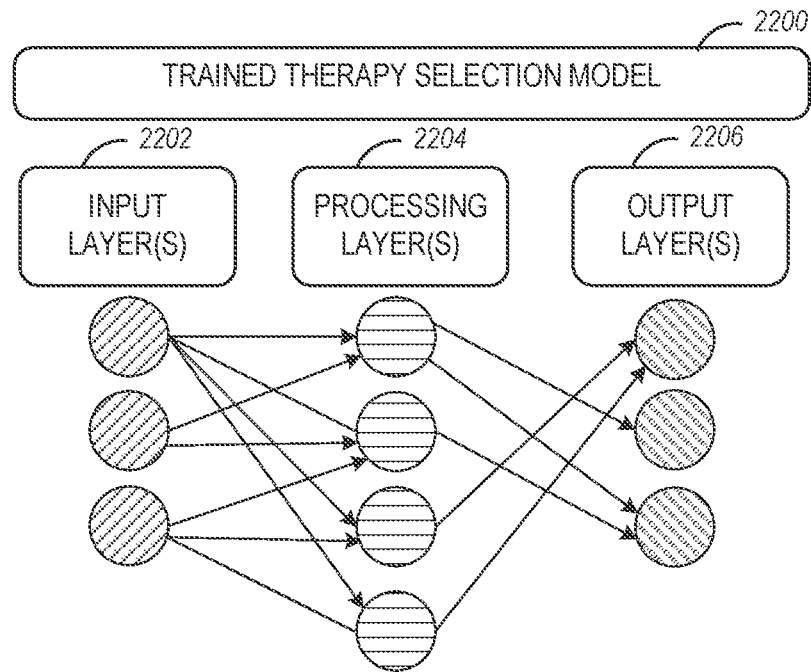
FIG. 22 illustrates a multi-layer model arrangement for evaluating physiological responses relative to media content, according to an example.

FIG. 22 illustrates an example multi-layer model arrangement for evaluating physiological responses relative to media content. Specifically, FIG. 22 illustrates a multi-layer model example 2200, having an inputs layer 2202, processing layer 2204, and output layer 2206. In various examples, such a multi-layer model may be used for, (1) assessment of psychological state from physiological data; (2) prediction of psychological state for use in exposure therapy and other commercial applications; or (3) unsupervised use to scan and assign predicted psychological data to novel media (e.g., media which is new to the model).

In the first example, the model of FIG. 22 is developed through the use of machine learning for performing the assessment of psychological state from physiological data using digital media devices and processing methods. For instance, physiological parameters are captured and used as inputs to a neural network model such as a multilayer perceptron, a generative adversarial network, a convolutional neural network, a deep reinforcement learning model, a recurrent neural network model such as a long short-term memory model or a similar neural network model or support vector machine, a genetic algorithm or decision trees or a random forest model. For all models, feature learning is used to identify discriminating factors for psychological state or anxiety level. For temporal features, inputs will be batched over time for relevant durations or models such as recurrent neural networks or convolutional neural network will be used so that the sequential or convolutional aspects of the network will act across the time dimension. Supervised and semi-supervised learning is used to facilitate future unsupervised learning. After training, the model will operate without patient self-reports or clinician assessment of psychological state to allow human independent characterization of state or anxiety score.

In the second example, an established model (such as the machine learning model of the first example) may be used for the assessment of novel media from physiological data. The trained model allows the establishment of a predicted psychological state for scenes and media during treatment while capturing physiological parameters for the novel media. The digital media device will be used to collect data while subjects are exposed to scenes or digital media works. After collection, the data will be used as inputs to the model to produce a predicted anxiety score that can be assigned to each scene or segment of the digital work. No self-assessments or other human inputs are needed for this assignment. This material then may be available as a source collection for use with exposure therapy or other commercial uses.

In the third example, an established model (such as the machine learning model of the first example) may be used for the assessment of novel media characteristics from physiological data using anxiety scoring device and methods. In this scenario, digital media is provided as an input to the machine learning model. The predicted psychological state or anxiety level is provided as an output of the machine learning model. A neural network model will be utilized such as a multilayer perceptron, a generative adversarial network, a convolutional neural network, a deep reinforcement learning model, a recurrent neural network model such as a long short-term memory model or a similar neural network model or support vector machine, a genetic algorithm or decision trees or a random forest model. For all models, feature learning will be used to identify discriminating audio and video features that predict psychological state. For temporal features, inputs are batched over time for relevant durations or models such as recurrent neural networks or convolutional neural network will be used so that the sequential or convolutional aspects of the network will act across the time dimension. Supervised and semi-supervised learning will be used to facilitate future unsupervised learning. The system will scan digital material including audio and visuals and assign predicted physiological states induced or associated with segments and scenes of novel semi supervised or unsupervised digital media. This media and its assigned predicted psychological state can then be used in future exposure therapy or other commercial uses. Following the assignment of predicted psychological state to novel media scenes and segments, active learning methods are used to test the predicted assignment. Sequences will be used as actual exposures with physiological data collection (as discussed in the second example, above). Specifically, scenes and segments that are nearest to the threshold may be identified by corroborating with viewing and data collection as in the second example above. An active learning method can also be used iteratively to improve the unsupervised scanning and assignment of psychological state to novel media scenes.

Figure 23:
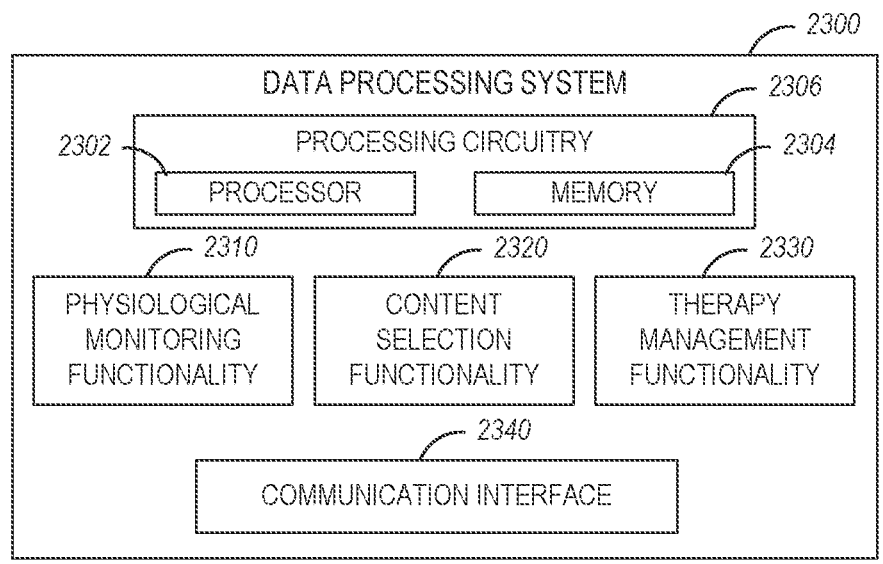
FIG. 23 illustrates a computer system implementation of a therapy selection system, used for performing any one of the methodologies discussed herein, according to an example.

FIG. 23 illustrates, by way of example, a block diagram of an embodiment of a data processing system 2300 (e.g., a computing system) implementing processing circuitry 2306 for use to implement a therapy selection system (e.g., system 106). The system 2300 may be operated by and embodied in a number of different computing platforms, such as in a server form factor, a workstation or personal computer form factor, a mobile computing device, etc. In some examples, the system 2300 may be a networked device connected via a network (or combination of networks) to a computing system operating a user interface computing system using a communication interface 2340. The network may include local, short-range, or long-range networks, such as Bluetooth, cellular, IEEE 802.11 (Wi-Fi), or other wired or wireless networks.

The system 2300 includes a processor 2302 and a memory 2304, which can be optionally included as part of processing circuitry 2306. The processor 2302 may be any single processor or group of processors that act cooperatively. The memory 2304 may be any type of memory, including volatile or non-volatile memory. The memory 2304 may include instructions, which when executed by the processor 2302, cause the processor 2302 to implement the features of the physiological monitoring functionality, content selection functionality, and therapy management functionality. Thus, the following references to electronic operations in the system 2300 or the processing circuitry 2306 may be performed by the processor 2302 or the circuitry 2306 as a whole.

For example, the processor 2302 or circuitry 2306 may implement any of the features of the methods 2000 or 2100 (or similar functions) for training a media content model, utilizing the media content model, and performing aspects of modulating physiological activity based on the model. These may be implemented using physiological monitoring functionality components or hardware 2310, content selection functionality components or hardware 2320, or therapy management functionality components or hardware 2330. The processor 2302 or circuitry 2306 may further provide data and commands to assist the processing and implementation of the programming using communication interface

2308. It will be understood that the processor 2302 or circuitry 2306 may also implement other aspects of the programming devices and device interfaces described above with reference to the user interfaces and functional operations of FIGS. 1 to 21.

Figure 24:
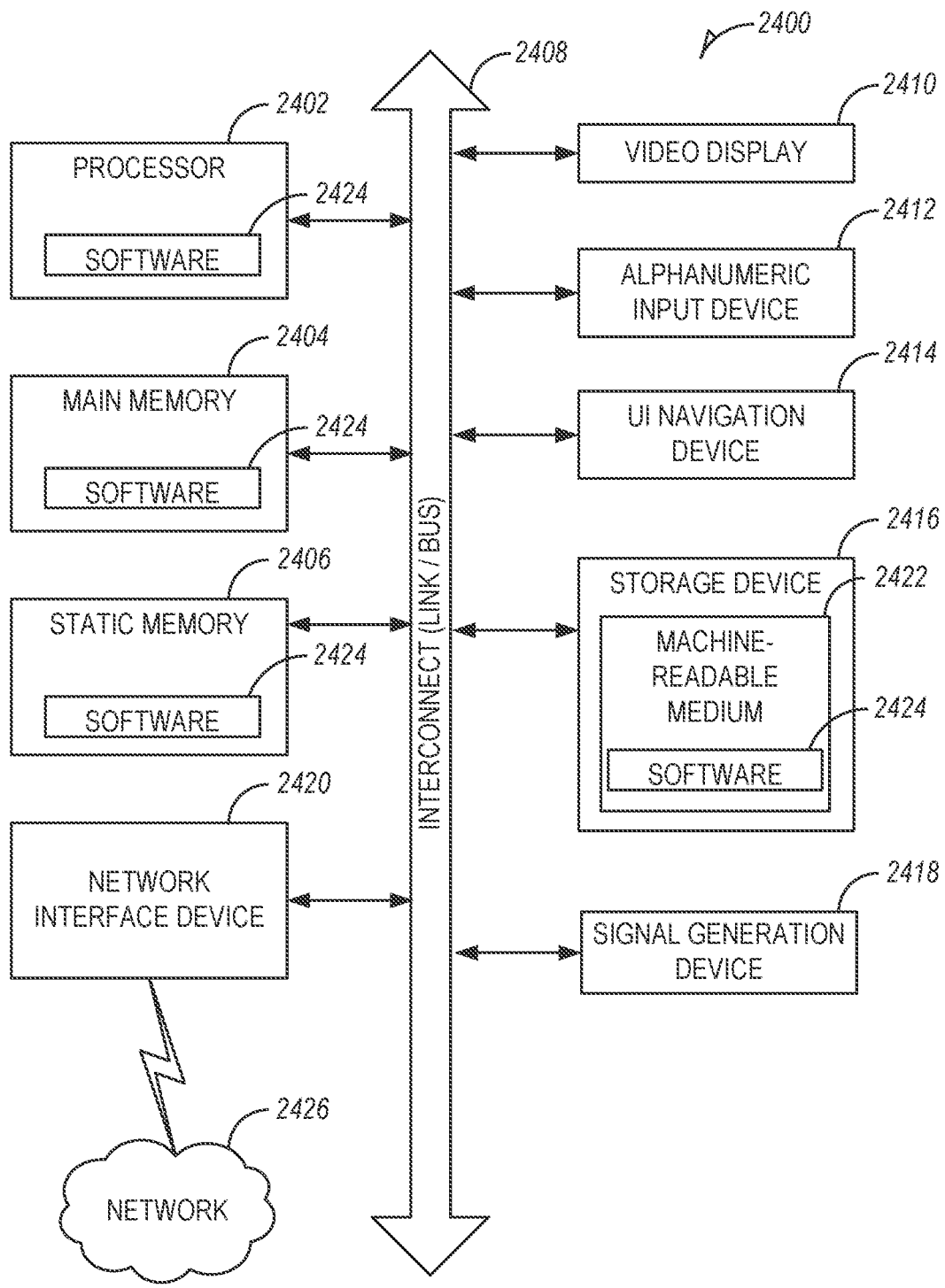
FIG. 24 is a block diagram illustrating a machine in the example form of a computer system, within which a set or sequence of instructions may be executed to cause the machine to perform any one of the methodologies discussed herein, according to an example.

FIG. 24 is a block diagram illustrating a machine in the example form of a computer system 2400, within which a set or sequence of instructions may be executed to cause the machine to perform any one of the methodologies discussed herein, according to an example embodiment. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The machine may be a personal computer (PC), a tablet PC, a hybrid tablet, a personal digital assistant (PDA), a mobile telephone, a medical device programmer, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. Similarly, the term "processor-based system" shall be taken to include any set of one or more machines that are controlled by or operated by a processor (e.g., a computer) to individually or jointly execute instructions to perform any one or more of the methodologies discussed herein.

Example computer system 2400 includes at least one processor 2402 (e.g., a central processing unit (CPU), a graphics processing unit (GPU) or both, processor cores, compute nodes, etc.), a main memory 2404 and a static memory 2406, which communicate with each other via an interconnect 2408 (e.g., link or bus). The computer system 2400 may further include a video display unit 2410, an alphanumeric input device 2412 (e.g., a keyboard), and a user interface (UI) navigation device 2414 (e.g., a mouse). In one embodiment, the video display unit 2410, input device 2412 and UI navigation device 2414 are incorporated into a touch screen display. The computer system 2400 may additionally include a storage device 2416 (e.g., a drive unit), a signal generation device 2418 (e.g., a speaker), a network interface device 2420, and one or more sensors (not shown), such as a global positioning system (GPS) sensor, compass, accelerometer, or other sensor. It will be understood that other forms of machines or apparatuses that are capable of implementing the methodologies discussed in this disclosure may not incorporate or utilize every component depicted in FIG. 24 (such as a GPU, video display unit, keyboard, etc.).

The storage device 2416 includes a machine-readable medium 2422 on which is stored one or more sets of data structures and instructions 2424 (e.g., software) embodying or utilized by any one or more of the methodologies or functions described herein. The instructions 2424 may also reside, completely or at least partially, within the main memory 2404, static memory 2406, and/or within the processor 2402 during execution thereof by the computer system 2400, with the main memory 2404, static memory 2406, and the processor 2402 also constituting machine-readable media.

While the machine-readable medium 2422 is illustrated in an example embodiment to be a single medium, the term "machine-readable medium" may include a single medium or multiple media (e.g., a centralized or distributed database, and/or associated caches and servers) that store the one or more instructions 2424. The term "machine-readable medium" shall also be taken to include any tangible (e.g., non-transitory) medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including but not limited to, by way of example, semiconductor memory devices (e.g., electrically programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks.

The instructions 2424 may further be transmitted or received over a communications network 2426 using a transmission medium via the network interface device 2420 utilizing any one of a number of well-known transfer protocols (e.g., HTTP). Examples of communication networks include a local area network (LAN), a wide area network (WAN), the Internet, mobile telephone networks, plain old telephone (POTS) networks, and wireless data networks (e.g., Wi-Fi, 3G, and 4G LTE/LTE-A or 5G networks). The term "transmission medium" shall be taken to include any intangible medium that is capable of storing, encoding, or carrying instructions for execution by the machine, and includes digital or analog communications signals or other intangible medium to facilitate communication of such software.

A first example may include the following and associated embodiments: A system, comprising: at least one processor; and at least one memory device comprising instructions, which when executed by the processor, causes the processor to perform operations that: select a sensory stimulus for delivery to a human subject, using a decision algorithm adapted to predict an expected physiological response signal to the sensory stimulus; monitor the human subject to obtain physiological response signals induced by delivery of the sensory stimulus; evaluate the physiological response signals induced by the delivery of the sensory stimulus; and control the delivery of the sensory stimulus, based on the evaluated physiological response signals relative to a desired outcome.

A second example may include the subject matter of the first example, wherein the system is adapted for modulating a cognitive state of the human subject, and wherein the desired outcome is a desired cognitive state.

A third example may include the subject matter of the first through second examples, wherein the system is adapted for modulating physiological activity of the human subject, and wherein the desired outcome is a desired physiological response.

A fourth example may include the subject matter of the third example, wherein the instructions further perform operations that: select a scene of media content, for presentation to the human subject, using the decision algorithm within a trained classification model, the trained classification model adapted to predict an expected physiological response to a stimulus in the scene of media content; obtain the physiological response signals from monitoring of the human subject during presentation of the scene of media content; evaluate the physiological response signals in response to the presentation of the scene of media content; and control the presentation of the scene of media content, based on the evaluated physiological response signals relative to the expected physiological response.

A fifth example may include the subject matter of the fourth example, that includes the instructions further to cause the processor to perform operations that: identify, based on the evaluated physiological response signals, a scaled response score, the scaled response score providing a measurement of the response to the stimulus from the presentation of the scene of media content; wherein the presentation of the scene of media content is controlled based on a comparison of the scaled response score to a goal response score for the human subject.

A sixth example may include the subject matter of the fifth example, wherein the comparison of the scaled response score to the goal response score is based on a comparison of at least one of: a target response magnitude occurring from presentation of the scene of media content, a target response decay occurring from presentation of the scene of media content, or a target response score occurring from presentation of the scene of media content.

A seventh example may include the subject matter of the fourth through sixth example, that includes the instructions further to cause the processor to perform operations that: obtain prior physiological response signals being obtained from before the presentation of the scene of media content; and wherein evaluating the physiological response signals is based on comparing the prior physiological response signals with the physiological response signals obtained during presentation of the scene of media content.

An eighth example may include the subject matter of the fourth through seventh example, wherein the scene of media content is selected based on a cognitive state goal for the human subject, and wherein the cognitive state goal defines a quantified cognitive state that is associated with a plurality of physiological measurements.

A ninth example may include the subject matter of the fourth through eighth example, wherein the classification model is trained based on a plurality of scenes of media content having corresponding physiological responses, and wherein the classification model is untrained on the scene of media content provided in the presentation to the human subject.

A tenth example may include the subject matter of the fourth through ninth example, wherein the scene of media content is selected from a media library based on a plurality of scene parameters corresponding to stimulus measurements, the scene parameters provided from among: intensity, duration, excitatory or sedative valence, or subject characteristics of the scene of media content.

An eleventh example may include the subject matter of the fourth through tenth example, wherein the physiological response signals are based on a plurality of signals obtained from monitoring the human subject with a respective plurality of sensors.

A twelfth example is a system for training a media content model, comprising: at least one processor; and at least one memory device comprising instructions, which when executed by the processor, causes the processor to perform operations that: capture physiological response signals from a human subject, the physiological response signals produced by exposing the human subject to a sensory stimulus; identify, from the physiological response signals, a response state of the human subject; and train a model to associate the response state with a scene of media content.

A thirteenth example may include the subject matter of the twelfth example, wherein the response state is a physiologic response state, and wherein the model is trained for analyzing a physiologic response of the human subject.

A fourteenth example may include the subject matter of the twelfth through thirteenth example, wherein the response state is a cognitive response state, wherein the model is trained for analyzing a cognitive response of the human subject.

A fifteenth example may include the subject matter of the fourteenth example, that includes the instructions further to cause the processor to perform operations that: train the model to associate the cognitive response state with a type of treatment.

A sixteenth example may include the subject matter of the fifteenth example, that includes the instructions further to cause the processor to perform operations that: monitor the human subject during presentation of the scene of media content, to identify the physiological response signals induced by the sensory stimulus; identify, from the physiological response signals, the cognitive response state of the human subject; and train the model to associate the cognitive response state with the scene of media content.

A seventeenth example may include the subject matter of the sixteenth example, wherein the scene of media content is provided from a video clip, with the instructions further to cause the processor to perform operations that identify the scene of media content from a portion of the video clip; and wherein the operations are performed with at least a second scene of the video clip, to train the model to associate a second identified cognitive response state with the second scene of the video clip.

An eighteenth example may include the subject matter of the sixteenth through seventeenth example, wherein the scene of media content is selected by a clinician as part of an identified treatment.

A nineteenth example may include the subject matter of the sixteenth through eighteenth example, wherein the association of the cognitive response state is established based on a plurality of scene parameters corresponding to the physiological response signals, the scene parameters provided from among: intensity, duration, excitatory or sedative valence, or subject characteristics of the scene of media content.

A twentieth example may include the subject matter of the sixteenth through nineteenth example, wherein the model is trained based on response characteristics of the physiological response signals, the response characteristics of the physiological response signals defining one or more of: peak of the response, magnitude of the response, direction of the response, valence of the response, time course of the response, transition of the response, and total measurement of the response.

Another example is a machine-readable medium including instructions, which when executed by a machine, cause the machine to perform the operations of any of the first through twentieth examples. Still another example is a method to perform the operations of any of the first through twentieth examples. Still yet another example is a system comprising respective means to perform the operations of any of the first through twentieth examples.

The above detailed description is intended to be illustrative, and not restrictive. The scope of the disclosure should, therefore, be determined with references to the appended claims, along with the full scope of equivalents to which such claims are entitled.

What is claimed is:

1. An audiovisual content selection system, comprising:
a sensor device comprising at least one physiological sensor, the at least one physiological sensor to capture physiological data from a human subject, the physiological data including multiple characteristics of at least one physiological measurement;
an output device comprising at least a display device and a speaker, the display device to output video to the human subject and the speaker to output audio to the human subject; and
a computing device communicatively coupled to the sensor device and the output device, the computing device comprising at least one processor to perform operations that:
identify a target pattern of autonomic nervous system activity to induce in the human subject, based on the captured physiological data;
obtain digital audiovisual data from a media library, the digital audiovisual data including at least one of video content or audio content;
process the digital audiovisual data with a trained artificial intelligence classification model, the classification model to identify expected physiological response signals of a predicted human to the at least one of the video content or the audio content, wherein the expected physiological response signals are identified in parallel by the classification model, and wherein the expected physiological response signals correspond to the multiple characteristics of the at least one physiological measurement;
select at least one of a video segment or an audio segment in the digital audiovisual data, based on the expected physiological response signals and the target pattern of autonomic nervous system activity;
cause the output device to provide an output of the digital audiovisual data including the at least one selected video segment or audio segment to the human subject;
monitor the human subject to observe physiological response signals induced from the output of the at least one selected video segment or audio segment, the physiological response signals including an observed pattern of autonomic nervous system activity in the physiological data captured during the output of the digital audiovisual data; and
automatically control the output of the digital audiovisual data to the human subject via the output device, based on a comparison of the observed pattern of autonomic nervous system activity to the target pattern of autonomic nervous system activity to achieve a physiologic response in the human subject.

2. The system of claim 1, the at least one processor to perform further operations that:
identify the target pattern of autonomic nervous system activity based on occurrence of a target physiological response of the human subject.

3. The system of claim 1, the at least one processor to perform further operations that:
identify, based on the observed pattern of autonomic nervous system activity, a scaled response score, the scaled response score providing a measurement of a response to the output of the at least one video segment or audio segment; and
automatically control the output of the digital audiovisual data based on a comparison of the scaled response score to a goal response score for the human subject.

4. The system of claim 3, wherein the comparison of the scaled response score to the goal response score is based on a comparison of at least one of: a target response magnitude occurring from the output of the at least one video segment or audio segment, a target response decay occurring from the output of the at least one video segment or audio segment, or a target response score occurring from the output of the at least one video segment or audio segment.

5. The system of claim 1, the at least one processor to perform further operations that:
obtain prior physiological data, the prior physiological data being obtained from the human subject before the output of the at least one video segment or audio segment;
wherein the operations to control the output of the digital audiovisual data to the human subject via the output device are further based on a comparison of the prior physiological data with the physiological data obtained during or after the output of the at least one video segment or audio segment.

6. The system of claim 1, the at least one processor to perform further operations that:
select the digital audiovisual data from the media library, using a decision algorithm.

7. The system of claim 1, wherein the at least one video segment or audio segment is selected based on a predefined goal for the human subject, and wherein the predefined goal is associated with a plurality of physiological measurements.

8. The system of claim 1, wherein the classification model is trained based on a plurality of segments of audiovisual content having corresponding physiological responses, and wherein the classification model is trained without use of the at least one video segment or audio segment to be output to the human subject.

9. The system of claim 1, wherein the at least one video segment or audio segment is provided in a scene selected from the media library based on a plurality of scene parameters corresponding to stimulus measurements, the plurality of scene parameters provided from among: intensity, duration, excitatory or sedative valence, or subject characteristics of the scene.

10. The system of claim 1, wherein the physiological data includes data collected from multiple physiological measurements of the human subject.

11. A non-transitory machine-readable storage medium comprising instructions, which when executed by at least one processor of a computing system, causes the computing system to perform operations that:
operably communicate with a sensor device and an output device, the sensor device comprising at least one physiological sensor to capture physiological data from a human subject, and the output device comprising at least a display device to output video to the human subject and a speaker to output audio to the human subject, the physiological data including multiple characteristics of at least one physiological measurement;
identify a target pattern of autonomic nervous system activity to induce in the human subject, based on the physiological data;
obtain digital audiovisual data from a media library, the digital audiovisual data including at least one of video content or audio content;
process the digital audiovisual data with a trained artificial intelligence classification model, the classification model to identify expected physiological response signals of a predicted human to the at least one of the video content or the audio content, wherein the expected physiological response signals are identified in parallel by the classification model, and wherein the expected physiological response signals correspond to the multiple characteristics of the at least one physiological measurement;

select at least one of a video segment or an audio segment in the digital audiovisual data, based on the expected physiological response signals and the target pattern of autonomic nervous system activity;

cause the output device to provide an output of the digital audiovisual data including the at least one selected video segment or audio segment to the human subject;

monitor the human subject to observe physiological response signals induced from the output of the at least one selected video segment or audio segment, the physiological response signals including an observed pattern of autonomic nervous system activity in the physiological data captured during the output of the digital audiovisual data; and automatically control the output of the digital audiovisual data to the human subject via the output device, based on a comparison of the observed pattern of autonomic nervous system activity to the target pattern of autonomic nervous system activity to achieve a physiologic response in the human subject.

12. The non-transitory machine-readable storage medium of claim 11, the instructions further to cause the at least one processor to perform operations that:

identify the target pattern of autonomic nervous system activity based on occurrence of a target physiological response of the human subject.

13. The non-transitory machine-readable storage medium of claim 11, the instructions further to cause the at least one processor to perform operations that:

identify, based on the observed pattern of autonomic nervous system activity, a scaled response score, the scaled response score providing a measurement of a response to the output of the at least one video segment or audio segment; and automatically control the output of the digital audiovisual data based on a comparison of the scaled response score to a goal response score for the human subject.

14. The non-transitory machine-readable storage medium of claim 13, wherein the comparison of the scaled response score to the goal response score is based on a comparison of at least one of: a target response magnitude occurring from the output of the at least one video segment or audio segment, a target response decay occurring from the output of the at least one video segment or audio segment, or a target response score occurring from the output of the at least one video segment or audio segment.

15. The non-transitory machine-readable storage medium of claim 11, the instructions further to cause the at least one processor to perform operations that:

obtain prior physiological data, the prior physiological data being obtained from the human subject before the output of the at least one video segment or audio segment;

wherein the operations to control the output of the digital audiovisual data to the human subject via the output device are further based on a comparison of the prior physiological data with the physiological data obtained during or after the output of the at least one video segment or audio segment.

16. The non-transitory machine-readable storage medium of claim 11, the instructions further to cause the at least one processor to perform operations that:

select the digital audiovisual data from the media library, using a decision algorithm.

17. The non-transitory machine-readable storage medium of claim 11, wherein the at least one video segment or audio segment is selected based on a predefined goal for the human subject, and wherein the predefined goal is associated with a plurality of physiological measurements.

18. The non-transitory machine-readable storage medium of claim 11, wherein the classification model is trained based on a plurality of segments of audiovisual content having corresponding physiological responses, and wherein the classification model is trained without use of the at least one video segment or audio segment to be output to the human subject.

19. The non-transitory machine-readable storage medium of claim 11, wherein the at least one video segment or audio segment is provided in a scene selected from the media library based on a plurality of scene parameters corresponding to stimulus measurements, the plurality of scene parameters provided from among: intensity, duration, excitatory or sedative valence, or subject characteristics of the scene.

20. The non-transitory machine-readable storage medium of claim 11, wherein the physiological data includes data collected from multiple physiological measurements of the human subject.

* * * * *